US009241508B2

(12) United States Patent
Kensler et al.

(10) Patent No.: US 9,241,508 B2
(45) Date of Patent: *Jan. 26, 2016

(54) NUTRITIONAL EMULSIONS COMPRISING CALCIUM HMB

(75) Inventors: Ann M. Kensler, Sugar Grove, OH (US); Paul Johns, Columbus, OH (US)

(73) Assignee: Abbott Laboratories, Abbott Park, IL (US)

(*) Notice: Subject to any disclaimer, the term of this patent is extended or adjusted under 35 U.S.C. 154(b) by 231 days.

This patent is subject to a terminal disclaimer.

(21) Appl. No.: 13/016,070

(22) Filed: Jan. 28, 2011

(65) Prior Publication Data

US 2011/0256301 A1 Oct. 20, 2011

Related U.S. Application Data

(60) Provisional application No. 61/299,649, filed on Jan. 29, 2010.

(51) Int. Cl.
| | | |
|---|---|---|
| *A23C 21/00* | (2006.01) | |
| *A23L 1/30* | (2006.01) | |
| *A23L 1/29* | (2006.01) | |
| *A23L 1/304* | (2006.01) | |
| *A23L 1/305* | (2006.01) | |
| *A23L 1/22* | (2006.01) | |

(52) U.S. Cl.
CPC . *A23L 1/30* (2013.01); *A23L 1/296* (2013.01); *A23L 1/304* (2013.01); *A23L 1/22083* (2013.01); *A23L 1/305* (2013.01); *A23L 1/3056* (2013.01); *A23V 2002/00* (2013.01)

(58) Field of Classification Search
CPC ....... A23L 1/22083; A23L 1/29; A23L 1/296; A23L 1/30; A23L 1/304; A23L 1/305; A23L 1/3056; A23V 2002/00; A23V 2250/628; A23V 2250/5114; A23V 2250/5488; A23V 2250/5424; A23V 2250/54246; A23V 2250/54252; A23V 2250/1842; A23V 2250/708; A23V 2250/702; A23V 2250/71; A23V 2250/712; A23V 2250/5036; A23V 2250/161; A23V 2250/16; A23V 2250/5054; A23V 2250/1618; A23V 2250/1578
USPC ............... 426/72, 73, 74, 580, 583, 601, 602, 426/613, 656, 657, 800, 801
See application file for complete search history.

(56) References Cited

U.S. PATENT DOCUMENTS

| | | | |
|---|---|---|---|
| 3,105,763 A | 10/1963 | North et al. | |
| 3,408,210 A | 10/1968 | Heyman | |
| 3,542,560 A | 11/1970 | Tomarelli et al. | |
| 4,104,290 A | 8/1978 | Koslowsky | |
| 4,259,358 A | 3/1981 | Duthie | |
| 4,742,081 A | 5/1988 | Stracher et al. | |
| 4,992,470 A | 2/1991 | Nissen | |
| 5,000,975 A | 3/1991 | Tomarelli | |
| 5,028,440 A | 7/1991 | Nissen | |
| 5,087,472 A | 2/1992 | Nissen | |
| 5,167,957 A | 12/1992 | Webb, Jr. et al. | |
| 5,171,442 A | 12/1992 | Nakshbendi | |
| 5,219,735 A | 6/1993 | Brule et al. | |
| 5,223,285 A | 6/1993 | DeMichele et al. | |
| 5,348,979 A | 9/1994 | Nissen et al. | |
| 5,360,613 A | 11/1994 | Nissen | |
| 5,374,657 A | 12/1994 | Kyle | |
| 5,431,928 A | 7/1995 | Saito et al. | |
| 5,444,054 A | 8/1995 | Garleb et al. | |
| 5,447,732 A | 9/1995 | Tanimoto et al. | |
| 5,457,130 A | 10/1995 | Tisdale et al. | |
| 5,492,938 A | 2/1996 | Kyle et al. | |
| 5,550,196 A | 8/1996 | Spence et al. | |
| 5,601,860 A | 2/1997 | Lien et al. | |
| 5,641,531 A | 6/1997 | Liebrecht et al. | |
| 5,726,146 A | 3/1998 | Almada et al. | |
| 5,780,451 A | 7/1998 | DeMichele et al. | |
| 5,834,427 A | 11/1998 | Han et al. | |
| 5,976,550 A | 11/1999 | Engel et al. | |
| 6,031,000 A | 2/2000 | Nissen et al. | |
| 6,060,446 A | 5/2000 | Zaloga et al. | |
| 6,080,788 A | 6/2000 | Sole et al. | |
| 6,096,358 A | 8/2000 | Murdick et al. | |
| 6,099,871 A | 8/2000 | Martinez | |
| 6,103,764 A | 8/2000 | Nissen | |
| 6,227,261 B1 | 5/2001 | Das et al. | |

(Continued)

FOREIGN PATENT DOCUMENTS

| | | |
|---|---|---|
| AU | 2006331950 A1 | 7/2007 |
| CA | 2632262 A1 | 7/2007 |
| CA | 2784605 | 6/2011 |
| CA | 2737972 | 10/2012 |
| CN | 1307478 | 8/2001 |
| CN | 1556772 | 12/2004 |
| CN | 101022818 | 8/2007 |
| CN | 101212961 | 7/2008 |
| CN | 101374509 | 2/2009 |
| CN | 101569412 | 11/2009 |

(Continued)

OTHER PUBLICATIONS

European Search Report for Application No. 11187274.3-1216, dated Feb. 15, 2012.

(Continued)

*Primary Examiner* — Leslie Wong
(74) *Attorney, Agent, or Firm* — Calfee, Halter & Griswold LLP

(57) ABSTRACT

Disclosed are nutritional emulsions comprising fat, carbohydrate, protein, and calcium HMB, wherein the nutritional emulsion has a weight ratio of a soluble calcium binding capacity to soluble calcium of from about 2.3 to about 12.0. Also disclosed are nutritional emulsions comprising fat, carbohydrate, protein, and calcium HMB, wherein the nutritional emulsion comprises less than 900 mg/L of soluble calcium in a weight ratio of calcium HMB to soluble calcium of from 6:1 to 15:1. The nutritional emulsions are surprisingly stable and generate minimal or no bitter flavors or after taste over time.

18 Claims, No Drawings

(56) References Cited

U.S. PATENT DOCUMENTS

| | | |
|---|---|---|
| 6,248,909 B1 | 6/2001 | Akimoto et al. |
| 6,291,525 B1 | 9/2001 | Nissen |
| 6,294,206 B1 | 9/2001 | Barrett-Reis et al. |
| 6,306,908 B1 | 10/2001 | Carlson et al. |
| 6,340,491 B1 | 1/2002 | Cain et al. |
| 6,365,218 B1 | 4/2002 | Borschel et al. |
| 6,371,319 B2 | 4/2002 | Yeaton et al. |
| 6,420,342 B1 | 7/2002 | Hageman et al. |
| 6,468,987 B1 | 10/2002 | Demichele et al. |
| 6,475,539 B1 | 11/2002 | DeWille et al. |
| 6,521,591 B1 | 2/2003 | Smeets et al. |
| 6,589,576 B2 | 7/2003 | Borschel et al. |
| 6,596,767 B2 | 7/2003 | Masor et al. |
| 6,620,427 B2 | 9/2003 | Lasekan et al. |
| 6,660,258 B1 | 12/2003 | Tovey |
| 6,749,881 B2 | 6/2004 | Kataoka et al. |
| 7,247,320 B2 | 7/2007 | Jost |
| 7,332,178 B2 | 2/2008 | Byard et al. |
| 7,419,596 B2 | 9/2008 | Dueppen et al. |
| 7,435,442 B2 | 10/2008 | Servotte |
| 7,445,807 B2 | 11/2008 | Lockwood |
| 7,498,026 B2 | 3/2009 | Dahlqvist et al. |
| 7,517,850 B2 | 4/2009 | Holt |
| 7,648,721 B2 | 1/2010 | Edens et al. |
| 7,795,204 B2 | 9/2010 | Gardiner et al. |
| 7,825,084 B2 | 11/2010 | Harris et al. |
| 8,217,077 B2 | 7/2012 | Baxter et al. |
| 8,916,217 B2 | 12/2014 | Johns et al. |
| 2001/0008641 A1 | 7/2001 | Krotzer |
| 2002/0035965 A1 | 3/2002 | Uni et al. |
| 2003/0092609 A1 | 5/2003 | Larsen et al. |
| 2003/0118703 A1 | 6/2003 | Nguyen et al. |
| 2003/0165604 A1 | 9/2003 | Tsubaki et al. |
| 2003/0203070 A1 | 10/2003 | Lin et al. |
| 2004/0013787 A1 | 1/2004 | Theuer |
| 2004/0048925 A1 | 3/2004 | Wiley et al. |
| 2004/0071825 A1 | 4/2004 | Lockwood |
| 2004/0106678 A1 | 6/2004 | Dobbins et al. |
| 2004/0122210 A1 | 6/2004 | Thim et al. |
| 2004/0202770 A1 | 10/2004 | Cain et al. |
| 2004/0220266 A1 | 11/2004 | Wiley et al. |
| 2004/0237466 A1 | 12/2004 | Grossmann et al. |
| 2004/0247755 A1 | 12/2004 | Doetsch et al. |
| 2004/0248771 A1 | 12/2004 | Raggi |
| 2005/0075280 A1 | 4/2005 | Larsen et al. |
| 2005/0106219 A1 | 5/2005 | Bortlik et al. |
| 2005/0215640 A1 | 9/2005 | Baxter et al. |
| 2005/0249650 A1 | 11/2005 | Damhuis et al. |
| 2006/0024385 A1 | 2/2006 | Pedersen |
| 2006/0193961 A1 | 8/2006 | Shastri et al. |
| 2006/0204632 A1 | 9/2006 | Barrett-Reis et al. |
| 2006/0286210 A1 | 12/2006 | Rangavajla et al. |
| 2006/0293220 A1 | 12/2006 | Holt |
| 2007/0093553 A1 | 4/2007 | Baxter et al. |
| 2007/0125785 A1 | 6/2007 | Robinson et al. |
| 2007/0142469 A1 | 6/2007 | Thomas et al. |
| 2007/0219146 A1 | 9/2007 | Bhaskaran et al. |
| 2008/0031860 A1 | 2/2008 | Hageman |
| 2008/0058415 A1 | 3/2008 | Shulman et al. |
| 2008/0119552 A1 | 5/2008 | Navarro |
| 2008/0193624 A1 | 8/2008 | Shulman et al. |
| 2008/0194407 A1 | 8/2008 | Ashmead et al. |
| 2008/0209864 A1 | 9/2008 | Fergusson et al. |
| 2008/0254153 A1 | 10/2008 | Wang et al. |
| 2008/0260923 A1 | 10/2008 | Kratky et al. |
| 2008/0274230 A1 | 11/2008 | Johns et al. |
| 2008/0305531 A1 | 12/2008 | Lam et al. |
| 2008/0317886 A1 | 12/2008 | Sparkman |
| 2009/0087540 A1 | 4/2009 | Haschke et al. |
| 2009/0110674 A1 | 4/2009 | Loizou |
| 2009/0142425 A1 | 6/2009 | Jager et al. |
| 2009/0220637 A1 | 9/2009 | Roessle |
| 2009/0263367 A1 | 10/2009 | Foley |
| 2010/0074969 A1 | 3/2010 | Hughes et al. |
| 2010/0179112 A1 | 7/2010 | Rathmacher et al. |
| 2011/0218244 A1 | 9/2011 | Kneller |
| 2011/0250322 A1 | 10/2011 | Johns et al. |
| 2011/0256272 A1 | 10/2011 | Johns et al. |
| 2011/0256297 A1 | 10/2011 | Johns |
| 2011/0256299 A1 | 10/2011 | Helmke et al. |
| 2011/0256301 A1 | 10/2011 | Kensler et al. |
| 2011/0305799 A1 | 12/2011 | Dewille et al. |
| 2012/0258209 A1 | 10/2012 | Ulstad |
| 2012/0283185 A1 | 11/2012 | Whyte |

FOREIGN PATENT DOCUMENTS

| | | |
|---|---|---|
| CN | 101574146 | 11/2009 |
| CN | 101703246 | 5/2010 |
| DE | 29707308 | 6/1997 |
| DE | 29709313 U1 | 9/1997 |
| DE | 10145818 C1 | 10/2002 |
| EP | 0036663 | 9/1981 |
| EP | 0367724 A1 | 9/1990 |
| EP | 0385859 A1 | 9/1990 |
| EP | 0756827 A2 | 2/1997 |
| EP | 698078 B1 | 8/1997 |
| EP | 0637239 B1 | 8/1999 |
| EP | 1762147 | 3/2007 |
| EP | 1968564 A2 | 9/2008 |
| EP | 2082738 A1 | 7/2009 |
| EP | 2461704 | 10/2013 |
| IN | 200800657 | 9/2009 |
| JP | 05503508 A | 6/1993 |
| JP | 7507569 T | 8/1995 |
| JP | 9121809 A | 5/1997 |
| JP | 11508282 T | 7/1999 |
| JP | 2001288107 A | 10/2001 |
| JP | 2002518440 A | 6/2002 |
| JP | 2002521428 A | 7/2002 |
| JP | 2003137790 A | 5/2003 |
| JP | 2006136318 | 6/2006 |
| JP | 2009155336 | 7/2009 |
| WO | 9406417 A1 | 3/1994 |
| WO | 9414429 A1 | 7/1994 |
| WO | 9739749 A2 | 10/1997 |
| WO | 9804253 A1 | 2/1998 |
| WO | 9966917 A2 | 12/1999 |
| WO | 0006134 A2 | 2/2000 |
| WO | 0015174 | 3/2000 |
| WO | 0107091 | 2/2001 |
| WO | 0156402 | 8/2001 |
| WO | 0158284 | 8/2001 |
| WO | 01/77271 A2 | 10/2001 |
| WO | 0217735 | 3/2002 |
| WO | 03053456 | 7/2003 |
| WO | 03091214 | 11/2003 |
| WO | 2004064715 A2 | 8/2004 |
| WO | 2005000315 | 1/2005 |
| WO | 2005102301 A2 | 11/2005 |
| WO | 2006/062424 A2 | 6/2006 |
| WO | 2007066232 A2 | 6/2007 |
| WO | 2007075605 A2 | 7/2007 |
| WO | 2007/098092 | 8/2007 |
| WO | 2008115723 | 9/2008 |
| WO | 2009/143097 A1 | 11/2009 |
| WO | 2011074995 | 6/2011 |
| WO | 2011094544 | 8/2011 |
| WO | 2011094548 | 8/2011 |
| WO | 2011094549 | 8/2011 |
| WO | 2011094551 | 8/2011 |
| WO | 2011094557 | 8/2011 |
| WO | 2011156238 | 12/2011 |
| WO | 2012088075 | 6/2012 |
| WO | 2012097064 | 7/2012 |
| WO | 2012109105 | 8/2012 |
| WO | 2012112419 | 8/2012 |

OTHER PUBLICATIONS

Kritchevsky, "An international symposium on cancer cachexia, cytokines, and EPA: Introduction," Nutrition, Elsevier Inc., U.S., vol. 12(1), p. S1 (1996).

(56) References Cited

OTHER PUBLICATIONS

Notice of Preliminary Rejection for Korean Application No. 10-2006-7022383, dated Feb. 13, 2012.
First Hearing Notice in Indian Application No. 1372/MUMNP/2008, dated Nov. 4, 2011.
Second Hearing Notice in Indian Application No. 1372/MUMNP/2008, dated Mar. 10, 2012.
Tisdale et al., "Inhibition of lipolysis and muscle protein degradation by epa in cancer cachexia," Nutrition, Elsevier Inc., U.S., vol. 12(1), pp. S31-S33 (1996).
Zuljdgeest-Van Leeuwen et al, "Inhibition of lipolysis by eicosapentaenoic acid in weight-losing cancer patients and healthy volunteers," Clinical Nutrition, Churchill Livingstone, London, G.B., vol. 17, p. 13 (1998).
Abbott, "HMB (Beta-hydroxy-beta-methylbutyrate): A Scientific Review," Apr. 2010, pp. 1-34, XP002670332, available at http://abbottnutrition.com/downloads/resourcecenter/hmb-a-scientific-review.pdf (last accessed Apr. 9, 2012).
"Lite Protein Drinks," Database GNPD (Online) Mintel, Mar. 2000, XP002670334, available at www.gnpd.com.
"Lite Protein Drink Mixes with GlycerLEAN," Database GNPD (Online) Mintel, Feb. 2002, XP002670335, available at www.gnpd.com.
"Lean DynamX," XP 002670342, available at http://www.fitpage.de/produicte/pd-1330122620.htm?categoryId=181 (last accessed Feb. 24, 2012) (5 pages total).
International Search Report and Written Opinion for International Application No. PCT/US2011/066096, dated Mar. 14, 2012.
Meletis et al., "Natural Supports for Gaining and Maintaining Muscle Mass," Alternative and Complementary Therapies, pp. 257-263 (2005).
Zhang et al., "Occurrence of beta-hydroxy-beta-methylbutyrate in foods and feeds," Faseb Journal, vol. 8(4-5), p. A464 (Abstract 2685) (1994).
English translation of Notice of Rejection in Japanese Application No. 2000-555603, dated Mar. 6, 2012.
Non-final Office Action for U.S. Appl. No. 13/016,059, dated Mar. 23, 2012.
English translation of Office Action for Taiwan Patent Application No. 095147808, dated Mar. 21, 2012.
Jagoe, "What do we really know about the ubiquitin-proteasome pathway in muscle atrophy?" Current Opinion in Clinical Nutrition and Metabolic Care, vol. 4, No. 3, pp. 183-190 (2001).
Meier, "Protein kinase C activation and its pharmacological inhibition in vascular disease," Vascular Medicine, vol. 5, No. 3, pp. 173-185 (2000).
Moscat, "NF-kappaB activation by protein kinase C isoforms and B-cell function," Embo Reports, vol. 4, No. 1, pp. 31-36 (2003).
O'Brianne et al., "The tumor promoter receptor protein kinase C: A novel target for chemoprevention and therapy of human colon cancer," Prog. Clin. Bio. Res., vol. 391, pp. 117-120 (1995).
Orino et al., "ATP-dependent reversible association of proteasomes with mutliple protein components to form 26S complexes that degrade ubiquitinated proteins in human HL-60 cells," FEBS Letters, vol. 284, No. 2, pp. 206-210 (1991).
Ostaszewski et al., "3-hydroxy-3-methylbutyrate and 2-oxoisocaproate effect body composition and cholestreol concentration in rabbits." Journal of Animal Physiology and Animal Nutrition, vol. 79, pp. 135-145 (1998).
Schols, "Evidence for a relation between metabolic derangements and increased levels of inflammatory mediators in a subgroup of patients with chronic obstructive pulmonary disease," Thorax, vol. 51, No. 8, pp. 819-824 (1996).
Schols, "Pulmonary cachexia," International Journal of Cardiology, vol. 85, No. 1, pp. 101-110 (2002).
Smart et al, "Polyclonal and allergen-induced cytokine responses in adults . . . " Journal of Allergy and Clinical Immunology, vol. 110, pp. 45-46 (2002).

Smith et al., "Effect of a cancer cachectic factor on protein synthesis/degradation in murine C2C12 myoblasts: modulation by eicosapentaenoic acid," Cancer Research, vol. 59, No. 21, pp. 5507-5513 (1999).
Smith et al., "Signal transduction pathways involved in proteolysis-inducing factor induced proteasome expression in murine myotubes," British Journal of Cancer, vol. 89, No. 9, pp. 1783-1788 (2003).
Takabatake et al., "Circulating leptin in patients with chronic obstructive pulmonary disease," American Journal of Respiratory and Critical Care Medicine, vol. 159, pp. 1215-1219 (1999).
Teixeira et al., "The role of interferon-c on immune and allergic responses . . . ," Mem. Inst. Oswaldo Cruz, vol. 100, pp. 137-144 (2005).
Todorov et al., "Characterization of a cancer cachectic factor," Nature, vol. 379, No. 6567, pp. 739-742 (1996).
Todorov et al., "Induction of muscle protein degradation and weight loss by a tumor product," Cancer Research, vol. 56, No. 6, pp. 1256-1261 (1996).
Toker, "Signaling through protein kinase C," Frontiers in Bioscience, vol. 3, pp. 1134-1147 (1998).
Van Koevering et al., "Effects of b-hydroxy-b-methylbutyrate on performance and carcass quality of feedlot steers." Journal of Animal Science, vol. 72, pp. 1927-1935 (1994).
Waalkes, "A fluorometric method for the estimation of tyrosine in plasma and tissues," Journal of Laboratory and Clinical Medicine, vol. 50, No. 5, pp. 733-736 (1957).
Watchorn et al., "Proteolysis-inducing factor regulates hepatic gene expression via the transcriptionfactor NF-kappaB and STAT3," FASEB Journal, vol. 15, No. 3, pp. 562-564 (2001).
Whitehouse et al., "Induction of protein catabolism in myotubes by 15(S)-hydroxyeicosatetraenoic acid through increased expression of the ubiquitin-proteasome pathway," British Journal of Cancer, vol. 89, No. 4, pp. 737-745 (2003).
Whitehouse et al., "Increased expression of the ubiquitin-proteosome pathway in murine myotubes by proteolysis-inducing factor (PIF) is associated with activation of the transcription factor NF-kappaB," British Journal of Cancer, vol. 89, No. 6, pp. 1116-1122 (2003).
Wolf et al., "The mitogen-activated protein kinase signaling cascade: from bench to bedside," IMAJ, vol. 4, No. 8, pp. 641-647 (2002).
Haumann, "Structured Lipids Allow Fat Tailoring," International News on Fats, Oils, and Related Materials, vol. 8(10), pp. 1004-1011 (1997).
Ho et al., "Antioxidants, NFkappaB activation and diabetogenesis," Proceedings of the Society for Experimental Biology and Medicine, vol. 222, No. 3, pp. 205-213 (1999).
Kutsuzawa et al., "Muscle energy metabolism and nutritional status in patients with chronic obstructive pulmonary disease," American Journal of Respiratory and Critical Care Medicine, vol. 152, No. 2, pp. 647-652 (1995).
Lorite et al., "Activation of A TP-ubiquita-dependent proteolysis in skeletal muscle in vivo and murine myoblasts in vitro by a proteolysis-inducing factor (PIF)," British Journal of Cancer, vol. 85, No. 2, pp. 297-302 (2001).
MERCK Index No. 1862, 2003.
MERCK Index No. 5198, 2003.
MERCK Index No. 7355, 2003.
MERCK Index No. 9908, 2003.
MERCK Index No. 9975, 2003.
Hanson, et al., "Seven days of muscle re-loading and voluntary wheel running following hindlimb suspension in mice restores running performance, muscle morphology and metrics of fatigue but not muscle strength," Muscle Res. Cell Motil., vol. 31, pp. 141-153 (2010).
International Search Report and Written Opinion for PCT/US2011/039170, dated Aug. 3, 2011.
Siu, et al., "Id2 and p53 participate in apoptosis during unloading-induced muscle atrophy," Am. J. Physiol. Cell. Physiol., vol. 288, C1058-C1073 (2005).
Ferrando, et al., "Prolonged bed rest decreases skeletal muscle and whole body protein synthesis," Am. J. Physiol. vol. 270, pp. E627-E633 (1996).

(56) References Cited

OTHER PUBLICATIONS

Kortebein, et al., "Effect of 10 days of Bed Rest on Skeletal Muscle in Healthy Older Adults," JAMA, vol. 297, pp. 1772-1774 (2007).
Zarzhevsky, et al., "Recovery of muscles of old rats after hindlimb immobilisation by external fixation is impaired compared with those of young rats," Exp. Gerontol., vol. 36, pp. 125-140 (2001).
Rham et al., "Role of Ionic Environment in Insolubilization of Whey Protein During Heat Treatment of Whey Products," Journal of Dairy Science, vol. 67(5), pp. 939-949 (1984).
Non-final Office Action for U.S. Appl. No. 13/151,911, dated Apr. 19, 2012.
Office Action issued in Philippines Patent Application No. 1-2008-501331, dated Apr. 4, 2012.
Office action issued in Chinese Patent Application No. 200580009596, dated Mar. 1, 2012.
Second Office Action issued in Japanese Patent Application No. 2007-504991, dated Mar. 13, 2012.
Examination Report issued in New Zealand Patent Application No. 599371, dated Apr. 20, 2012.
International Preliminary Report on Patentability for International Application No. PCT/US2011/022938, dated Jan. 25, 2012.
International Preliminary Report on Patentability for International Application No. PCT/US2011/022947, dated Feb. 15, 2012.
Office Action issued in U.S. Appl. No. 13/016,005, dated Jun. 1, 2012.
Examiner's First Report in Australian Patent Application No. 2006331950, dated Apr. 19, 2012.
Anonymous, "Reload Dietary Supplements," Database GNPD (Online) Mintel, May 2010, XP002676291, available at www.gnpd.com.
Charbonneau, "Recent case histories of food product-metal container interactions using scanning electron microscopy-x-ray microanalysis," Scanning, vol. 19(7), pp. 512-518 (1997).
International Search Report and Written Opinion for International Application No. PCT/US2012/024817, dated Jun. 6, 2012.
International Search Report and Written Opinion for International Application No. PCT/US2012/023767, dated Jun. 6, 2012.
Montanari et al., "Quality of Organic Coatings for Food Cans: Evaluation Techniques and Prospects of Improvement," Progress in Organic Coatings, vol. 29(1-4), pp. 159-165 (1996).
Final Office Action for U.S. Appl. No. 13/016,041, dated Jun. 8, 2012.
English translation of Office Action issued in Chinese Patent Application No. 201110084963, dated Mar. 30, 2012.
Kreider, et al., "Effect of Calcium Beta-Hydroxy-Beta-Methylbutyrate (HMB) Supplementation During Resistance-Training on Markers of Catabolism Body Compositon and Strength," International Journal of Sports Medicine, vol. 20, No. 8, pp. 503-509 (Nov. 1, 1999).
International Search Report and Written Opinion for PCT/US2011/022928 (May 23, 2011).
International Search Report and Written Opinion for PCT/US2011/022932 (May 23, 2011).
International Search Report and Written Opinion for PCT/US2011/022938 (May 23, 2011).
International Search Report and Written Opinion for PCT/US2011/022947 (May 23, 2011).
International Search Report and Written Opinion for PCT/US2011/022935 (May 23, 2011).
de Maat, et al., "Inflammation, Thrombosis and Atherosclerosis: Results of the Glostrup Study," Journal of Thrombosis and Haemostasis, 2003, vol. 1, No. 5, p. 950-957.
Choi, et al., "Hematein inhibits atherosclerosis by inhibition of reactive oxygen generation and NF-kappaB-dependent inflammatory mediators in hyperlipidemic mice," Journal of Cardiovascular Pharmacology, 2003, vol. 42, No. 2, p. 287-295.
May, Patricia Eubanks, "Reversal of cancer-related wasting using oral supplementation with a combination of beta-hydroxy-beta-beta-methylbutyrate, arginine, and glutamine," American Journal of Surgery, vol. 183, No. 4, 2002, p. 471-479.
European Search Report and Opinion for Application No. 10186645.7-1216, dated Feb. 14, 2011.
Office Action from Indian Patent Application No. 1372/MUMNP/2008, dated Sep. 23, 2010.
Office Action issued in Taiwan Application No. 094109357, dated Jun. 24, 2011.
Sult, "Th1/Th2 Balance: A Natural Therapeutic Approach to Th2 Polarization in Allergy," Applied Nutritional Science Reports, 2003, p. 1-8.
AIDS Alert, 1999, vol. 14, No. 4, p. 41-43.
Clark, et al., "Nutritional treatment for acquired immunodeficiency virus-associated wasting using beta-hydroxy beta-methylbutyrate, glutamine, and arginine: a randomized, double-blind, placebo-controlled study," Journal of Parenteral and Enteral Nutrition, May 2000, vol. 24, No. 3, p. 133-139.
Ostaszewski, et al. "3-hydroxy-3-methylbuyric acid (HMB) in immunological reactions generated by nutritional allergy in guinea pigs," Veterinary Medicine, vol. 51, No. 2, 1995 (translation).
Office Action issued in Japanese Application No. 2007-504991, dated Jun. 21, 2011.
Office Action issued in Russian Application No. 2008129605, dated Jul. 5, 2011.
Examiner's First Report issued for New Zealand Patent Application No. 593182, dated Jun. 3, 2011.
Smith, et al., "Attenuation of Proteasome-Induced Proteolysis in Skeletal Muscle by B-hydroxy-B-methylbutyrate in Cancer-Induced Muscle Loss," Cancer Research, 2005, vol. 65(1), p. 277-283.
Aggarwal et al., "Suppression of the Nuclear Factor kB Activation Pathway by Spice-Derived Phytochemicals: Reasoning for Seasoning", Annals of the New York Academy of Science, vol. 1030, pp. 434-441 (2004).
Barber et al., "The effect of an oral nutritional supplement enriched with fish oil on weight-loss in patients with pancreatic cancer," British Journal of Cancer, 1999, pp. 80-86, vol. 81, No. 1.
Barnes et al., "NF-kappa B: a pivotal role in asthma and a new target for therapy", Trends in Pharmacological Sciences, 1997, pp. 46-50, vol. 18.
Beck et al., "Anticachectic and Antitumor Effect of Eicosapentaenoic Acid and Its Effect on Protein Turnover," Cancer Research, vol. 51, pp. 6089-6093 (1991).
Brennan et al., "Nitrogen Metabolism in Cancer Patients," Cancer Treatment Reports, vol. 65, Supplemental 5, pp. 67-78 (1981).
Evans et al., "Expression and activation of protein kinase C in eosinophils after allergen challenge," Am J Physiol Lung Cell Mole Physiol, vol. 277, pp. 233-239 (1999).
Examination Report for Malaysian App. PI20082097 dated Jul. 29, 2011.
Examination Report from NZ Patent Application No. 568611, dated Apr. 13, 2010.
Flakoll et al., "Effect of b-hydroxy-b-methylbutyrate, arginine and lysine supplementation on strength, functionality, body composition, and protein metabolism in elderly women," Nutrition, vol. 20, pp. 445-451 (2004).
Fuller et al., "Decreasing male broiler mortality by feeding the leucine catabolite b-hydroxy-b-methylbutyrate," Poult. Sci., vol. 73, Supplemental 1, p. 93 (1994).
Gallagher et al., "B-hydroxy-b-methylbutyrate ingestion, Part 1: Effects on strength and fat free mass," Med. Sci. Sports Exerc, vol. 32, No. 12, pp. 2109-2115 (2000).
Gallagher et al., "b-hydroxy-b-methylbutyrate ingestion, Part II: effects on hematology, hepatic and renal function," Med. Sci. Sports Exerc., vol. 32, No. 12, pp. 2116-2119 (2000).
HMB, www.interactivenutrition.com, last visited Dec. 29, 2004.
International Search Report and Written Opinion for PCT/US2005/007951, dated Aug. 24, 2006.
International Search Report and Written Opinion for PCT/US2006/048303, dated May 6, 2008.
Jowko et al., "Creatine and b-hydroxy-b-methylbutyrate (HMB) additively increase lean body mass and muscle strength during a weight-training program", Nutrition, vol. 17, pp. 558-566 (2001).
Juven product information, http://abbottnutrition.com/Products/Juven, 5 pages, dated 2010.
Kaizen HMB, www.bodybuilding.com, last visited Dec. 29, 2004.

(56) References Cited

OTHER PUBLICATIONS

Kisner, "The Nutrition of the Cancer Patient," Cancer Treatment Reports, vol. 65, Supplemental 5, pp. 1-2 (1981).
Knitter et al., "Effects of b-hydroxy-b-methylbutyrate on muscle damage after a prolonged run," J. Appl. Physiol., vol. 89, pp. 1340-1344 (2000).
Lentsch et al., "Activation and Regulation of NFkB during Acute Inflammation," Clin. Chem. Lab. Med., vol. 37, No. 3, pp. 205-208 (1999).
Levenhangen et al., "Arginine, Lysine, and b-hydroxymethylbutyrate (HMB) Supplementation Enhances the Efficiency of Protein Synthesis in Elderly Females," Nutrition Week Abstracts, vol. 75, pp. 411S-412S (2002).
Macchi et al., "Influence of co-ingestion of glucose on b-hydroxy-b-methylbutyrate (HMB) metabolism in humans," FASEB J., p. A909 (1999).
Miller et al., "The effect of intensive training and b-hydroxy-b-methylbutyrate (HMB) on the physiological response to exercise in horses." FASEB J., p. A290 (1997).
Milne et al., "Do Routine Oral Protein and Energy Supplements Improve Survival and Reduce Length of Hospital Stay for Elderly People," Nutrition Week Abstracts, p. 412S (2002).
Moschini et al., "Effect of feeding b-hydroxy-b-methylbutyrate (HMB) on leucine and fat metabolism in mammary gland," FASEB J., p. A70 (1993).
Nissen et al., "b-hydroxy-b-methylbutyrate (HMB) supplementation in humans is safe and may decrease cardiovascular risk factors," J. Nutr., vol. 130, pp. 1937-1945 (2000).
Nissen et al., "Colostral milk fat percentage and pig performance are enhanced by feeding the leucine metabolite b-hydroxy-b-methylbutyrate to sows," J. Anim. Sci., vol. 72, pp. 2331-2337 (1994).
Nissen et al., "Effect of b-hydroxy-b-methylbutyrate (HMB) supplementation of strength and body composition of trained and untrained males undergoing intense resistance training," FASEB J., p. A287 (1996).
Nissen et al., "Effect of dietary supplements on lean mass and strength gains with resistance exercise: A meta analysis," J. Appl. Physiol., vol. 94, pp. 651-659 (2003).
Nissen et al., "Effect of feeding b-hydroxy-b-methylbutyrate (HMB) on body composition and strength of women," FASEB J., p. A150 (1997).
Nissen et al., "Effect of leucine metabolite b-hydroxy-b-methylbutyrate on muscle metabolism during resistance-exercise training," J. Appl. Physiol., vol. 81, No. 5, pp. 2095-2104 (1996).
Nissen et al., "Nutritional role of the leucine metabolite b-hydroxy-b-methylbutyrate (HMB)," J. Nutr. Biochem., vol. 8, pp. 300-311 (1997).
Nissen et al., "The effect of b-hydroxy-b-methylbutyrate on growth, mortality and cacass qualitiies of broiler chickens," Poultry Science, vol. 71, pp. 137-155 (1994).
Nissen et al., "The effects of the leucine catabolite, b-hydroxy-b-methylbutyrate (HMB), on the growth and health of growing lambs," J. Anim. Sci., p. 243 (1994).
Nonnecke et al., "Leucine and its Catabolites After Mitogen-Stimulated DNA Synthesis by Bovine Lymphocytes," J. Nutr., vol. 121, pp. 1665-1672 (1991).
Office Action for U.S. Appl. No. 11/025,466, dated Oct. 4, 2010.
Office Action for U.S. Appl. No. 11/025,466, dated Dec. 5, 2008.
Office Action for U.S. Appl. No. 11/025,466, dated Apr. 14, 2010.
Office Action for U.S. Appl. No. 11/025,466, dated Apr. 6, 2011.
Office Action for U.S. Appl. No. 11/025,466, dated May 5, 2008.
Office Action for U.S. Appl. No. 11/025,466, dated Jun. 25, 2009.
Office Action for U.S. Appl. No. 11/025,466, dated Aug. 17, 2007.
Office Action for U.S. Appl. No. 11/025,466, dated Sep. 8, 2011.
Office Action for U.S. Appl. No. 11/641,978, dated Oct. 20, 2009.
Office Action for U.S. Appl. No. 11/641,978, dated Feb. 26, 2008.
Office Action for U.S. Appl. No. 11/641,978, dated Mar. 3, 2009.
Office Action for U.S. Appl. No. 11/641,978, dated Jun. 7, 2010.
Office Action from Chinese Patent Application No. 200680047936.3, dated Feb. 24, 2011.
Office Action from Chinese Patent Application No. 200680047936.3, dated May 25, 2010.
Office action issued in Chinese App. No. 200580009569.0, dated Jun. 28, 2010.
Office action issued in Taiwan App. No. 094109357, dated Dec. 2, 2010.
Oliver et al., "Airway Smooth Muscle and Asthma," Allergology International, vol. 55, pp. 215-223 (2006).
Ostaszewski et al., "3-Hydroxy-3-Methylbutyrate (HMB) Fed in the Water Enhance Immune Response in Young Broilers," Abstract 96.
Ostaszewski et al., "The immunomodulating activity of dietary 3-hydroxy-3-methylbutyrate (HMB) in weaning pigs,"J. Anim. Sci., vol. 81, Supplemental 1, p. 136 (1998).
Ostaszewski et al., "The leucine metabolite 3-hydroxy-3-methylbutyrate (HMB) modifies protein turnover in muscles of laboratory rates and domestic chickens in vitro," J Anim. Physiol. A. Anim. Nutr. 84, pp. 1-8 (2000).
Ostaszewski et al., "The effect of the leucine metabolite 3-hydroxy 3-methylbutyrate (HMB) on muscle protein synthesis and protein breakdown in chick and rat muscle," Journal of Animal Science, vol. 74, Supplemental 1, p. 138 (1996).
Ostaszewski et al., "Dietary supplementation of 3-hydroxy-3-methylbutyrate improved catch-up growth in underfed lambs," Ann. Zootech, vol. 43, p. 308 (1994).
Panton et al., "Effect of b-hydroxy-b-methylbutyrate and resistance training on strength and functional ability in the elderly," Medicine & Science in Sports & Exercise, p. S194 (1998).
Panton et al., "Nutritional supplementation of the leucine metabolite b-hydroxy-b-methylbutyrate (HMB) during resistance training," Nutrition, vol. 16, pp. 734-739 (2000).
Papet et al., "The effect of a high dose of 3-hydroxy-3-methylbutyrate on protein metabolism in growing lambs," Br. J. Nutr., vol. 77, pp. 885-896 (1997).
Perkins et al., "Good cop, bad cop: the different faces of NF-kB,"Cell Death and Differentiation, vol. 13, pp. 759-772 (2006).
Peterson et al., "Enhancement of cellular and humoral immunity in young broilers by the dietary supplementation of b-hydroxy-b-methylbutyrate," Immunopharmacology and Immunotoxicity, vol. 21, No. 2, pp. 307-330 (1999).
Peterson et al., "In Vitro Exposure with B-Hydroxy-B-Methylbutyrate Enhances Chicken Macrophage Growth and Function," Vetrinary Immunology and Immunopathology, vol. 67, pp. 67-78 (1999).
Porter et al., "Sustained NFAT Signaling Promotes a Th1-like Pattern of Gene Expression in Primary Murine CD4+ T Cells," Journal of Immunology, vol. 168, pp. 4936-4945 (2002).
Rathbacher et al., "Safety of a nutritional mixture of b-hydroxy-b-methylbutyrate (HMB), glutamine and arginine in healthy young adults and patients with AIDS," JPEN 23(1): S10 (1999).
Rathmacher et al., "The effect of the leucine metabolite b-hydroxy-b-methylbutyrate on lean body mass and muscle strength during prolonged bedrest," FASEB J., p. A909.
Rothmacher et al., "Supplementation with a combination of beta-hydroxy-beta-methylbutyrate (HMB), arginine, and glutamine is safe and could improve hematological parameters," Journal of Parenteral and Enternal Nutrition, vol. 28, No. 2, p. 6575 (2004).
Sandberg et al., "Effect of b-hydroxy-b-methylbutyrate on the physiological response to exercise and conditioning in horses," Journal of Animal Science, p. 198 (1997).
Sandberg et al., "The Effect of Intensive Training and b-hydroxy-b-methylbutyrate (HMB) on Muscle Glycogen concentration in the Horse," Journal of Animal Science, vol. 76, Supplemental 1, p. 175 (1998).
Siwicki et al., "Immunomodulating effect of 3-hydroxy-3-methylbutyrate (HMB) on the nonspecific cellular and humaoral defense mechanisms in rainbow trout (*Oncorhynchus nykiss*)," Journal of Animal Science, vol. 76, Supplemental 1, p. 137, (1998).
Siwicki et al., "In Vitro Effects of 3-Hydroxy-3-methylbutyrate (HMB) on measures of immune function and immunocompetence in fish," Journal of Animal Science, vol. 76, Supplemental 1, p. 136 (1998).

(56) References Cited

OTHER PUBLICATIONS

Siwicki et al., "Influence of 3-hydroxy-3-methylbutyrate on specific cellular immune response after in vitro and in vivo immunization with Yersinia ruckeri antifen," Journal of Animal Science, vol. 76, Supplemental 1, p. 136 (1998).
Smith et al., "Mechanisms of the attentuation of proteolysis-inducing factor stimulated protein degradation in muscle by beta-hydroxy-beta-methylbutyrate." Cancer Research, pp. 8731-8735 (2004).
Talleyrand et al., "Effect of feeding b-hydroxy-b-methylbutyrate on immune function in stressed calves," FASEB J, p. A951 (1994).
Talleyrand et al., "Uptake and output of the leucine metabolite b-hydroxy-b-methylbutyrate (HMB) across the legs of pigs," FASEB J., p. A71 (1993).
Tisdale et al., "Inhibition of Weight Loss by w-3 Fatty Acids in an Experimental Cachexia Model," Cancer Research, vol. 50, pp. 5002-5026 (1990).
Van Koevering et al., "Effect of b-hydroxy-b-methylbutyrate on the health and performance of shipping-stressed calves," The Oklahoma State Animal Science Research Report, pp. 312-316 (1993).
Van Koevering et al., "Oxidation of leucine and a-ketoisocaproate to b-hydroxy-b-methylbutyrate in vivo," American Journal of Physiology, pp. E27-E31 (1992).
Vukovich et al., "Body composition of 70-year-old adults responds to dietary beta-hydroxy beta-methylbutyrate similarly to that of young adults," Journal of Nutrition, vol. 131, No. 7, pp. 2049-2052 (2001).
Vukovich et al., "Effect of beta-hydroxy beta-methylbutyrate on the onset of blood lactate accumulation and VO2 peak in endurance-trained cyclists," J. Strength & Conditioning Res., vol. 15, No. 4, pp. 491-497 (2001).
Vukovich et al., "The effect of dietary b-hydroxy-b-methylbutyrate (HMB) on strength gains and body composition in older adults," FASEB J., p. A376 (1997).
Williams et al., "Effect of a specialized amino acid mixture on human collagen deposition," Annals of Surgery, vol. 236, No. 3, pp. 369-375 (2002).
Witte et al., "Nutritional abnormalities contributing to cachexia in chronic illness," International Journal of Cardiology, vol. 85, pp. 23-31 (2002).
Zachwieja et al., "Effect of the Leucine Metabolite b-hydroxy-b-methylbutyrate on muscle protein synthesis during prolonged bedrest," FASEB Abstracts, p. A1025 (1999).
Zhang et al., "Change in plasma b-hydroxy-b-methylbutyrate (HMB) by feeding leucine, a-ketiusicaoriate and isovaleric acid to pigs," FASEB J., p. A392 (1993).
Examination Report for Vietnam Application No. 1-2006-01765, issued Aug. 18, 2011.
Andela, et al., "NFkappaB: a pivotal transcription factor in prostate cancer metastasis to bone," Clinical Orthopaedics and Related Research, vol. 415S, pp. S75-S85 (2003).
Andrews, et al. "A rapid micropreparation technique for extraction of DNA-binding proteins from limiting numbers of mammalian cells," Nucleic Acids Res., vol. 19, No. 9, p. 2499 (1991).
Battaini, "Protein kinase C isoforms as therapeutic targets in nervous systemdisease states," Pharmacological Research, vol. 44, No. 5, pp. 353-361 (2001).
Bibby et al., "Characterization of the transplantable adenocarcinoma of the mouse colon producing cachexia in recipient animals," J. Natl. Cancer Inst., vol. 78, No. 3, pp. 539-546 (1987).
Carter, "Protein Kinase C as a drug target: Implications for drug or diet prevention and treatment of cancer," Current Drug Targets, vol. 12, No. 2, pp. 163-183 (2000).
Coffman et al.,"Syntheses by Free-radical Reactions. V. A New Synthesis of Carboxylic Acids", J. Am. Chem. Soc., vol. 80, pp. 2282-2887 (1958), submitted 1957.
Delfino, "Hormonal Regulation of the NF-kappaB signaling pathway," Molecular and Cellular Endocrinology, vol. 157, Nos. 1-2, pp. 1-9 (1999).
Dentener et al., "Systemic anti-inflammatory mediators in COPD: increase in soluble interleukin 1 receptor II during treatment of exacerbations," Thorax, vol. 56, No. 9, pp. 721-726 (2001).

Examiner's 2nd Report issued in New Zealand Application No. 568611, dated Jun. 3, 2011.
Fenteany et al., "Lactacystin, proteasome function and cell fate," J. Biol. Chem., vol. 273, No. 15, pp. 8545-8548 (1998).
Frank, "Potential new medical therapies for diabetic retinopathy: protein kinase C inhibitors," American Journal of Opthamology, vol. 133, No. 5, pp. 693-698 (2002).
Goekijan, "Protein kinase C in the treatment of disease: Signal transduction pathways, inhibitors, and agents in development," Current Medical Chemistry, vol. 6, No. 9, pp. 877-903 (1999).
Gomes-Marcondes et al., "Development of an in-vitro model system to investigate the mechanism of muscle protein catabolism induced by proteolysis-inducing factor," British Journal of Cancer, vol. 86, No. 10, pp. 1628-1633 (2002).
Office Action issued in U.S. Appl. No. 13/016,005, dated Jan. 27, 2012.
Office Action issued in U.S. Appl. No. 13/016,041, dated Feb. 3, 2012.
Office Action issued in U.S. Appl. No. 11/025,466, dated Feb. 10, 2012.
Ballard et al., "Effect of I-glutamine supplementation on impaired glucose regulation during intravenous lipid administration," Nutrition, vol. 12(5), pp. 349-354 (1996).
Clinical Infectious Diseases, vol. 25(2), p. 457 (1997).
Elam et al., "Effects of arginine and ornithine on strength, lean body mass and urinary hydroxyproline in adult males," The Journal of Sports Medicine and Physical Fitness, vol. 29(1), pp. 52-56 (1989).
Fligger et al., "Arginine Supplementation Increases Weight Gain, Depresses Antibody Production, and Alters Circulating Leukocyte Profiles in Preruminant Calves Without Affecting Plasma Growth Hormone Concentrations," J. Anim. Sci., vol. 75, pp. 3019-3025 (1997).
Jarowski et al., "Utility of Fasting Essential Amino Acid Plasma Levels in Formulation of Nutritionally Adequate Diets III: Lowering of Rat Serum Cholesterol Levels by Lysine Supplementation," Journal of Pharmaceutical Sciences, vol. 64(4), pp. 690-691 (1975).
Office Action issued in Chinese Application No. 200580009596.0, dated Jun. 9, 2011.
Office Action issued in Japanese Application No. 2000-555603, dated Jan. 12, 2010.
Office Action issued in Japanese Application No. 2000-555603, dated Feb. 15, 2011.
Office Action issued in Japanese Application No. 2000-555603, dated Oct. 25, 2011.
Office Action issued in Philippines Application No. 12006501893, dated Oct. 11, 2011.
Campbell, et al., "Allergic humans are hyporesponsive to a CXCR3 ligand-mediated Th1 immunity-promoting loop," The FASEB Journal, vol. 18, pp. 329-331 (2004).
Hauber, et al., "Expression of interleukin-4, interleukin-9 and interleukin-13 in peripheral blood mononuclear cells of cystic fibrosis patients with and without allergy," EXCLI Journal, vol. 5, pp. 209-216 (2006).
Office Action issued in Canadian Patent Application No. 2,560,042, dated Nov. 14, 2011.
Office Action issued in Russian Application No. 2008129605, dated Aug. 12, 2011.
Merck Manual, "Starving and Wasting," 16th Ed., pp. 919-920 (1995).
Gaurav, P., "Japan Ensure Wave-3 Replicate Report and Recommendation for Clinical Manufacture" (Apr. 28, 2009).
Golubitskii, et al., "Stability of Ascorbic Acid in Aqueous and Aqueous-Organic Solutions for Quantitative Determination," J. Anal Chem., vol. 62, No. 8, pp. 742-747 (2007).
Puspitasari, et al., "Calcium Fortification of Cottage Cheese with Hydrocolloid Control of Bitter Flavor Defects," J. Dairy Sci., vol. 74, pp. 1-7 (1991).
Toelstede et al., "Sensomics Mapping and Identification of the Key Bitter Metabolites in Gouda Cheese," J Agric Food Chem, vol. 56, pp. 2795-2804 (2008).

(56) References Cited

OTHER PUBLICATIONS

Toelstede et al., "Quantitative Studies and Taste Re-Engineering Experiments Toward the Decoding of the Nonvolatile Sensometabolome of Gouda Cheese," J Agric Food Chem, vol. 56, pp. 5299-5307 (2008).
Tordoff, et al., "Vegetable Bitterness is Related to Calcium Content," Appitite, vol. 52, pp. 498-504 (2009).
Engel, et al., "Evolution of the Composition of a Selected Bitter Camembert Cheese During Ripening: Release and Migration of Taste-Active Compounds," J. Agric Food Chem, vol. 49, pp. 2940-2947 (2001).
Engel, et al., "Evolution of the Taste of a Bitter Camembert Cheese During Ripening: Characterization of a Matrix Effect," J. Agric Food Chem., vol. 49, pp. 2930-2939 (2001).
Gacs, et al., "Significance of Ca-Soap Formation for Calcium Absorption in the Rat," Gut, vol. 18, pp. 64-68 (1977).
Technical Information: HEC-3000 10-Step Water Purification System, Home Environment Center.
Case Study: Water Purification Plant Installed at New UK Power Station, Filtration & Separation (Dec. 2004).
Written Opinion from PCT/US2005/007951 dated Oct. 6, 2006.
International Search Report and Written Opinion for PCT/US2012/020941 dated Apr. 26, 2012.
Response to Office Action for U.S. Appl. No. 13/016,005 dated Apr. 27, 2012.
Amendment and Response with RCE for U.S. Appl. No. 13/016,005 dated Aug. 3, 2012.
Applicant-Initiated Interview Summary for U.S. Appl. No. 13/016,005 dated Sep. 6, 2012.
Non-final office action for U.S. Appl. No. 13/016,005 dated Mar. 28, 2013.
Office action in U.S. Appl. No. 13/016,248 dated Nov. 7, 2012.
Notice of Allowance for U.S. Appl. No. 13/016,248 dated Apr. 22, 2013.
International Search Report for PCT/US2005/007951 dated Oct. 26, 2006.
Amendment with RCE for U.S. Appl. No. 13/016,041 dated Sep. 4, 2012.
Applicant-Initiated Interview Summary for U.S. Appl. No. 13/016,041 dated Sep. 5, 2012.
Office Action from U.S. Appl. No. 13/016,041 dated Apr. 1, 2013.
Amendment A for U.S. Appl. No. 13/016,059 dated Jun. 25, 2012.
Office Action for U.S. Appl. No. 13/016,248 dated Nov. 7, 2012.
Amendment to Office Action for U.S. Appl. No. 13/016,248 dated Feb. 7, 2013.
Amendment and Response to Office Action for U.S. Appl. No. 13/151,911 dated Jul. 19, 2012.
Office Action from U.S. Appl. No. 13/151,911 dated Nov. 9, 2012.
Amendment from U.S. Appl. No. 13/151,911 dated Feb. 11, 2013.
Office action in U.S. Appl. No. 13/440,610 dated Apr. 11, 2013.
Response to office action for U.S. Appl. No. 13/440,610 dated Apr. 23, 2013.
Office Action for U.S. Appl. No. 13/440,610 dated May 9, 2013.
First Office Action from Chilean Application No. 192-2011 dated Apr. 24, 2013.
Notice of Allowance in EP Application No. 11705722.4 dated Nov. 15, 2012.
Intention to Grant in EP Application No. 11705724.0 dated Nov. 29, 2012.
Communication from EP Application No. 11705725.7 dated Sep. 5, 2012.
Communication from EP Application No. 11707733.9 dated Sep. 5, 2012.
Response to Communication from EP Application No. 11707733.9 dated Mar. 6, 2013.
First Examination Report in EP Application No. 11726580.1 dated Jan. 21, 2013.
Search Report in EP Application No. 12382138.1 dated Jun. 14, 2012.
Extended Search Report in EP Application No. 12382138.1 dated Oct. 16, 2012 (13 pages).
Translation of Notice of Rejection for Japanese Patent Application No. 2008-547409 dated Jun. 5, 2012.
Alon et al., "Supplementing with beta-hydroxy-beta-methylbutyrate (HMB) to build and maintain muscle mass: a review," Research Communications in Molecular Pathology and Pharmacology, vol. 111 (1-4), pp. 139-151 (2002).
"Body Core Strength" ("Calorie Facts"), pub. online Apr. 25, 2010. http://web.archive.org/web/20100425070417/http://bodycorestrength.com/calorie-facts/.
Burke, R., "Inhibition of mitogen-activated protein kinase and stimulation of Akt kinase signaling pathways: Two approaches with therapeutic potential in the treatment of neurodegenerative disease," Pharm. and Therap., vol. 114 (3), pp. 261-277 (2007).
"Calorie Counter" (Calories in Infant Formula, Abbott Nutrition, Similac, ADVANCE with iron, liquid concentrate, not reconstituted), pub. online Jan. 17, 2010. http://web.archive.org/web/20100117072138/http://acaloriecounter.com/food/infant-formula-abbott-nutrition-similac-advance-wth-iron-liquid-concentrated-not-reconstituted-formerly-ross-.
The Dairy Council ("The Nutritional Composition of Diary Products"), pub. online Jul. 2007—see pp. 3,5, and 7. The nutrional information from the 2002 summary edition of the Composition of Foods (Food Standards Agency (2002)) McCance and Widdowson's The Composition of Foods, 6th Summary Edition).
Damjanac et al., "Dissociation of Akt/PKB and ribosomal S6 kinase signaling markers in a transgenic mouse model of Alzheimer's disease," Neurobiology of Disease, vol. 29(2), pp. 354-367 (2008).
De Los Reyes, et al., "Overview of resistance training, diet, hormone replacement and nutritional supplements on age-related sarcopenia-a minireview," Res. Comm. in Mol. Path. and Pharm., vol. 113-114, pp. 159-170, (2003).
"Milk Composition Proteins", "Milk Composition & Synthesis Resource Library", pub. online Oct. 19, 2009. http://web.archive.org/web/20091019072335/http://classes.ansci.illinois.edu/ansc438/milkcompsynth/milkcomp_protein_html.
Kornasio et al., "Beta hydroxy-beta-methylbutyrate (HMB) stimulates myogenic cell proliferation, differentiation and suvival via the MAPK/ERK and PI13K/Akt pathways," Biochimica et Biophysica Acta Molecular Cell Research, vol. 1793(5), pp. 755-763 (2009).
MacDonald et al., "Understanding and Managing Cancer Cachexia,", Journal of the American College of Surgeons, vol. 197(1), 2003, pp. 143-161.
Nawa et al., "A novel Akt/PKB-interacting protein promotes cell adhesion and inhibits familial amyotrophic lateral sclerosis-linked mutant SOD1-induced neuronal death via inhibition of PP2A-mediated dephosphorylation of Akt/PKB," Cellular Signalling, vol. 20(3), pp. 493-505 (2008).
Portal et al., "Effect of HMB supplementation on body composition, fitness, hormonal profile and muscle damage indices," J. of Ped. Endo. & Meta., vol. 23(7), pp. 641-650 (2010).
Tanaka et al., "Effects of the novel Foxo 1 inhibitor AS1708727 on plasma glucose and trigyceride levels in diabetic db/db mice," Euro. Jour. of Pharm., vol. 645(1-3), pp. 185-191 (2010).
Von Bockelmann, Bernhard et al., "Aseptic Packaging of Liquid Food Products: A Literature Review", Journal of Agricultural and Food Chemistry, May 1986, vol. 34, Issue 3, pp. 384-392.
"Yahoo Answers" ("What age did you start giving your baby whole milk ?"), pub. online 2008. http://answers.yahoo.com/question/index?qid=20080819094659AA0urJT.
Zdychova et al., "Emerging role of Akt Kinase/Protein Kinase B signaling in pathophysiology of diabetes and its complications," Physiol. Res. vol. 54(1), pp. 1-16 (2005).
Intention to Grant in EP Application No. 11705723.2 dated Apr. 25, 2013.
Amendment A to U.S. Appl. No. 13/016,041 dated May 2, 2012.
Google search—"How much fat is in skim milk ?" http://www.google.com/...=how+much+fat+is+in+skim&gs . . . , last accessed May 3, 2013.
English translation of 1st Office Action for Chinese Application No. 201180006376.8 dated May 13, 2013.

(56) References Cited

OTHER PUBLICATIONS

Decision to Grant in EP Application No. 11705724.0 dated Jun. 13, 2013.
Applicant-Initiated Interview Summary for U.S. Appl. No. 13/016,005 dated Jul. 29, 2013.
Amendment and Response to Office Action for U.S. Appl. No. 13/016,005 dated Jul. 29, 2013.
Final Office action for U.S. Appl. No. 13/016,005 dated Sep. 12, 2013.
Response to OA for U.S. Appl. No. 13/440,610 dated Aug. 9, 2013.
English translation of First Office Action for Chinese Application No. 201180007418.x (PCT/US2011/022938) dated Jun. 7, 2013.
English translation of First Office Action for Chinese Application No. 201180007420.7 (PCT/US2011/022932) dated Jun. 5, 2013 (received Jul. 5, 2013).
English translation of First Office Action for CN Application No. 201180007682.3 dated May 31, 2013 (received Jul. 8, 2013).
English translation for First Office Action for CN Application No. 201180007700.8 dated May 28, 2013 (received Jul. 10, 2013).
Huai, Ming Yan, "Progress in 2-4 methionine hydroxy butyric acid (HMB)," Foreign Animal Husbandry (Pigs and Poultry), Jun. 2003.
Rowlands, et al., "Effects of b-hydroxy-b-methylbutyrate supplementation during resistance training on strength, body composition, and muscle damage in trained and untrained young men: a meta-anlysis," J. of Strength and Conditioning Research, 23(3) 2009, pp. 836-846.
Shen Hua, "Development in the aseptic package", China Packaging Industry Mar. 31, 2006.
Xu Sheng, "Evaluation of hydrogen peroxide sterilization in aseptic packaging systems", Beverage Industry, vol. 9, Issue 7 Dec. 31, 2006.
Extended Search Report in EP Application No. 11187274.3 dated Jun. 28, 2012.
Office Action in EP Application No. 11187274.3 dated Aug. 6, 2012.
Response after Final with Terminal Disclaimer in U.S. Appl. No. 13/016,005 filed Dec. 9, 2013.
Non Final Office Action for U.S. Appl. No. 13/016,005 dated Dec. 27, 2013.
Notice of Abandonment for U.S. Appl. No. 13/016,041 dated Oct. 21, 2013.
Amendment with RCE, Affidavit for U.S. Appl. No. 13/151,911 dated Oct. 18, 2013.
Final Office Action in U.S. Appl. No. 13/440,610 dated Dec. 6, 2013.
Reexamination Notice from Chinese Application No. 200580009596.0 dated Jul. 9, 2013.
English translation of First Office Action for CN Application No. 201180028614.5 (PCT/US2011/039170) (05174) dated Oct. 11, 2013 (received Nov. 20, 2013).
English translation of 2nd Office Action in Chinese Application No. 201180006376.8 dated Jan. 13, 2014.
English translation of Second Office Action for Chinese Application No. 20118007420.7 dated Jan. 16, 2014.
Intention to Grant in EP Application No. 11705722.4 dated Jan. 3, 2014.
Communication from EP Application No. 11705725.7 dated Jan. 24, 2014.
Intention to Grant in EP Application No. 11707733.9 dated Dec. 18, 2013.
Communication in EP Application No. 11726580.1 dated Dec. 10, 2013.
First Substantive Examination Report for SA Application No. 111320139 received Dec. 19, 2013.
Examination Report for SG Application 201208825-8 dated Oct. 30, 2013.
Response to Office Action for U.S. Appl. No. 13/016,005 dated Mar. 20, 2014.
Office Action dated Apr. 10, 2014 acknowledging entry of Mar. 20, 2014 response to Dec. 27, 2013 Office Action for U.S. Appl. No. 13/016,005.
Final Office Action in U.S. Appl. No. 13/016,005 dated Apr. 10, 2014.
Office action issued in Canadian Application No. 2,785,522 dated May 1, 2014.
Office action issued in Canadian Application No. 2,785,523 dated May 21, 2014.
Office action issued in Canadian Application No. 2,785,528 dated May 14, 2014.
Office Action in Canadian Application No. 2,801,339 dated May 26, 2014,
English Translation of Second Office Action for CN Application No. 201180028614.5 (PCT/US2011/039170) dated May 20, 2014.
English translation of Second Office Action for Chinese Application No. 20118007418.x (PCT/US2011/022938) dated Mar. 24, 2014.
English translation of Third Office Action for Chinese Application No. 20118007420.7 dated May 15, 2014.
Second Office Action for CN Application No. 20118007682.3 dated Mar. 18, 2014.
English translation of Second Office Action for Chinese Application No. 201180007700.8 dated Feb. 8, 2014 (received Mar. 13, 2014).
Decision to Grant in EP Application No. 11705722.4 dated Apr. 25, 2014.
Decision to Grant in EP Application No. 11707733.9 dated May 15, 2014.
Communication in EP Application No. 11726580.1 dated Mar. 24, 2014.
Gao Fucheng et al., "Microcapsulation granulation Technology," New and High Technology of Modern Food Engineering, China Light Industry Press, pp. 51-53 and 58 (May 31, 1997), with summary in English on final page.
Applicant-Initiated Interview Summary in U.S. Appl. No. 13/016,005 dated Jun. 19, 2014.
Response in U.S. Appl. No. 13/016,005 dated Aug. 6, 2014.
Final Office Action in U.S. Appl. No. 13/016,005 dated Aug. 20, 2014.
Non Final Office Action for U.S. Appl. No. 13/016,059 dated Jul. 16, 2014.
Response for U.S. Appl. No. 13/016,059 dated Sep. 24, 2014.
Non final Office Action for U.S. Appl. No. 13/151,911 dated Jul. 14, 2014.
Response with RCE in U.S. Appl. No. 13/440,610 dated Mar. 6, 2014.
Non final office action for U.S. Appl. No. 13/440,610 dated Sep. 3, 2014.
Office action in Canadian Application No. 2,785,524 dated Jul. 28, 2014.
Office action in Canadian Application No. 2,785,526 dated Aug. 15, 2014.
Intention to Grant in EP Application No. 11705725.7 dated Jul. 11, 2014.
Office Action in JP Application No. 2012-551324 dated Aug. 5, 2014.
Office Action in JP Application No. 2012-551322 dated Aug. 5, 2014.
Office Action in MX Application No. MX/a/2012/008783 dated Sep. 12, 2014.
Office Action in MX Application No. MX/a/2012/008785 mailed Aug. 29, 2014.
Office Action in MX Application No. MX/a/2012/008786 mailed Sep. 3, 2014.
English translation of Office Action and Search Report in TW Application No. 100103536 dated Jun. 30, 2014.
http://www.pedialyte.com/thisispedialyte/variety.cfm dated Jul. 2004.
http://www.pediasure.com/homepage.cfm dated Mar. 2005.
Notice of Appeal in U.S. Appl. No. 13/016,005 dated Nov. 20, 2014.
Appeal Brief for U.S. Appl. No. 13/016,005 dated Jan. 29, 2015.
English translation of second Office Action in TW Application No. 100103536 dated Oct. 17, 2014.
Final office action in U.S. Appl. No. 13/016,059 dated Jan. 20, 2015.
Notice of Allowance in U.S. Appl. No. 13/016,248 dated Oct. 7, 2014.
Response to Office Action for U.S. Appl. No. 13/151,911 dated Oct. 14, 2014.
Office Action for U.S. Appl. No. 13/151,911 dated Nov. 6, 2014.
Response with RCE in U.S. Appl. No. 13/151,911 dated Feb. 20, 2015.
Applicant-Initiated Interview Summary and Advisory Action for U.S. Appl. No. 13/151,911 dated Mar. 5, 2015.

(56) References Cited

OTHER PUBLICATIONS

Response to Mar. 5, 2015 Advisory Action for U.S. Appl. No. 13/151,911 dated Mar. 6, 2015.
Applicant-Initiated Interview in U.S. Appl. No. 13/440,610 dated Dec. 10, 2014.
Request for Reconsideration after Non-Final Rejection in U.S. Appl. No. 13/440,610 dated Jan. 5, 2015.
Final Office Action in U.S. Appl. No. 13/440,610 dated Jan. 30, 2015.
English translation of Third Office Action for CN Application No. 201180028614.5 dated Sep. 29, 2014.
Decision of Rejection for CN Application No. 20118007418.x dated Jan. 16, 2015.
English translation of Fourth Office Action for Chinese Application No. 20118007420.7 dated Dec. 1, 2014.
English translation of Third Office Action for Chinese Application No. 20118007700.8 dated Aug. 21, 2014 (received Sep. 25, 2014).
Decision to Grant in EP Application No. 11705725.7 dated Dec. 18, 2014.
Intention to Grant in EP Application No. 11726580.1 dated Sep. 18, 2014.
Decision to Grant in EP Application No. 11726580.1 dated Feb. 5, 2015.
EESR in EP 14169084.2 dated Sep. 22, 2014.
Office Action in JP Application No. 2012-551325 date Sep. 2, 2014.
Office Action in JP Application No. 2012-551326 dated Sep. 2, 2014.
Office Action in JP Application No. 2012-551329 dated Sep. 2, 2014.
Office Action in JP Application No. 2013-514238 mailed Nov. 11, 2014.
Gharsallaoui et al., "Applications of spray-drying in microencapsulation of food ingredients: An overview,", Food Research International, 40 (2007) pp. 1107-1121.
Office Action for CA Application No. 2,801,339 dated Feb. 27, 2015.
Response to Notification of Non-Compliant Appeal Brief in U.S. Appl. No. 13/016,005 dated Apr. 2, 2015.

NUTRITIONAL EMULSIONS COMPRISING CALCIUM HMB

This application claims the benefit of U.S. Provisional Application No. 61/299,649 filed Jan. 29, 2010

FIELD OF THE DISCLOSURE

The present disclosure relates to nutritional emulsions comprising calcium beta-hydroxy-beta-methylbutyrate (calcium HMB).

BACKGROUND OF THE DISCLOSURE

Beta-hydroxy-beta-methylbutyrate (HMB) is a naturally occurring amino acid metabolite that is often formulated into a variety of nutritional products and supplements. HMB is commonly used in such products to help build or maintain muscle mass and strength in selected individuals.

HMB is a metabolite of the essential amino acid leucine and has been shown to modulate protein turnover and inhibit proteolysis. In most individuals, muscle converts approximately 5% of available leucine to HMB, thus producing about 0.2 to 0.4 grams of HMB per day in a 70 kg male. In studies where various kinds of stress were induced in animals, HMB supplementation increased lean mass. Clinical studies also suggest that HMB has at least two functions in recovery from illness or injury including protection of lean mass from stress-related damage and enhancement of protein synthesis. It has been suggested that HMB may also be useful in enhancing immune function, reducing the incidence or severity of allergy or asthma, reducing total serum cholesterol and low density lipoprotein cholesterol, increasing the aerobic capacity of muscle, and other uses.

Since HMB is most often used in individuals to support the development and maintenance of muscle mass and strength, many HMB products have been formulated with additional nutrients that may also be helpful in promoting healthy muscle. Some of these HMB products contain additional nutrients such as fat, carbohydrate, protein, vitamins, minerals and so forth. Calcium HMB is a commonly used form of HMB when formulated into oral nutritional products, which products include tablets, capsules, reconstitutable powders, and nutritional liquids and emulsions. Nutritional emulsions are particularly useful in this regard because such emulsions may contain a balance of fat, protein, carbohydrates, vitamins, and minerals, all of which are useful for helping maintain healthy muscle.

It has now been found, however, that nutritional emulsions containing calcium HMB are often not physically stable over time, that such emulsions are not readily stable with many protein systems, and that protein-containing and other sediment forms in the emulsions during or after formulation, especially when packaged and stored for extended periods of time.

It has also been discovered that these nutritional emulsions containing calcium HMB often develop an undesirably bitter off flavor or after taste after the emulsion has been packaged and stored for extended periods of at least 1-3 months.

There is therefore a need for nutritional emulsions comprising calcium HMB that remain physically stable during shelf life and do not develop a bitter flavor or after taste over time.

SUMMARY OF THE DISCLOSURE

One embodiment of the present disclosure is directed to a nutritional emulsion comprising fat, carbohydrate, protein, and calcium HMB, wherein the nutritional emulsion has a weight ratio of a soluble calcium binding capacity to total soluble calcium of from about 2.3 to about 12.0.

Another embodiment of the present disclosure is directed to a nutritional emulsion comprising fat, carbohydrate, protein, and calcium HMB, wherein the nutritional emulsion comprises less than 900 mg/L of soluble calcium in a weight ratio of calcium HMB to soluble calcium of from 6:1 to 15:1.

It has been found that the addition of calcium HMB to nutritional emulsions can result in the development of a bitter flavor or after taste, which typically does not manifest until the product is manufactured, packaged, and stored for a period of at least about 1 to about 3 months. Indeed, it has been found that nutritional emulsions comprising calcium HMB often produce little or no bitter flavor or after taste when consumed immediately or within about 1 month, including from about 1 to about 3 months, after formulation, but that such bitter flavor or after taste surprisingly develops in the packaged product over time.

It has also been found that many nutritional emulsions comprising calcium HMB are physically unstable, often resulting in the collection of excessive protein-containing and or other sediments at the bottom of the emulsion container, thus reducing nutrient availability as well as the effective shelf-life of the product.

It has now also been found that these instability and or flavor issues can be minimized or eliminated by selectively reducing the availability of solubilized calcium in the formulation by formulating with a weight ratio of a soluble calcium binding capacity as defined herein to total soluble calcium of from about 2.3 to about 12.0.

It has also been found that such reductions can also be achieved by formulating the nutritional emulsion with less than 900 mg/L of solubilized calcium in a weight ratio of calcium HMB to solubilized calcium of from 6:1 to 15:1.

DETAILED DESCRIPTION OF THE DISCLOSURE

The nutritional emulsions of the present disclosure comprise calcium HMB and at least one ingredient, feature, or element to inhibit the development of bitter flavor or after taste and or to improve product stability over shelf life. The essential features of the nutritional emulsions, as well as some of the many optional variations and additions, are described in detail hereafter.

The term "calcium HMB" as used herein, unless otherwise specified, refers to the calcium salt of beta-hydroxy-beta-methylbutyrate (also referred to as beta-dydroxyl-3-methyl butyric acid, beta-hydroxy isovaleric acid, or HMB), which is most typically in a monohydrate form. All weights, percentages, and concentrations as used herein to characterize calcium HMB are based on the weight of calcium HMB monohydrate, unless otherwise specified.

The term "nutritional emulsion" as used herein, unless otherwise specified, refers to liquid emulsions comprising fat, protein, and carbohydrate which are suitable for oral administration to a human.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "shelf stable" as used herein, unless otherwise specified, refers to a nutritional emulsion that remains commercially stable after being packaged and contained within a hermetically sealed container and then stored at 18-24° C. for at least 3 months, including from about 6 months to about 24 months, and also including from about 12 months to about 18 months.

The term "pH stable" as used herein, unless otherwise specified, means that the pH is resistant or at least more resistant to pH reductions due to a buffering effect of HMB.

The term "plastic" as used herein, unless otherwise specified, means food grade plastics approved by the U.S. Food and Drug Administration or other suitable regulatory group, some non-limiting examples of which include polyvinyl chlorides, polyethylene terephthalate, high density polyethylene, polypropylenes, polycarbonates, and so forth.

The terms "sterile", "sterilized" and "sterilization" as used herein, unless otherwise specified, refer to the reduction in transmissible agents such as fungi, bacteria, viruses, spore forms, and so forth, in food or on food grade surfaces to the extent necessary to render such foods suitable for human consumption. Sterilization processes may include various techniques involving the application of heat, peroxide or other chemicals, irradiation, high pressure, filtration, or combinations or variations thereof.

All percentages, parts and ratios as used herein, are by weight of the total composition, unless otherwise specified. All such weights as they pertain to listed ingredients are based on the active level and, therefore, do not include solvents or by-products that may be included in commercially available materials, unless otherwise specified.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various embodiments of the nutritional emulsions of the present disclosure may also be substantially free of any optional or selected essential ingredient or feature described herein, provided that the remaining nutritional emulsion still contains all of the required ingredients or features as described herein. In this context, and unless otherwise specified, the term "substantially free" means that the selected nutritional emulsion contains less than a functional amount of the optional ingredient, typically less than about 0.5%, including less than about 0.1% and also including zero percent, by weight of such optional or selected essential ingredient.

The nutritional emulsions and corresponding manufacturing methods of the present disclosure can comprise, consist of, or consist essentially of the essential elements of the disclosure as described herein, as well as any additional or optional element described herein or otherwise useful in nutritional emulsion formula applications.

Product Form

The nutritional emulsions of the present disclosure are aqueous emulsions comprising fat, protein, and carbohydrate. These emulsions are flowable or drinkable liquids at from about 1 to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf-stable. The nutritional emulsions typically contain up to about 95% by weight of water, including from about 50% to about 95%, also including from about 60% to about 90%, and also including from about 70% to about 85%, of water by weight of the nutritional emulsions.

The nutritional emulsions may be formulated with sufficient kinds and amounts of nutrients so as to provide a sole, primary, or supplemental source of nutrition, or to provide a specialized nutritional emulsion for use in individuals afflicted with specific diseases or conditions. These nutritional emulsions may thus have a variety of product densities, but most typically have a density greater than about 1.055 g/ml, including from 1.06 g/ml to 1.12 g/ml, and also including from about 1.085 g/ml to about 1.10 g/ml.

The nutritional emulsions may have a caloric density tailored to the nutritional needs of the ultimate user, although in most instances the emulsions comprise from about 100 to about 500 kcal/240 ml, including from about 150 to about 350 kcal/240 ml, and also including from about 200 to about 320 kcal/240 ml. These nutritional emulsions also comprise calcium HMB as described hereinafter, the amount of which most typically ranges from about 0.4 to about 3.0 g/240 ml, including from about 0.75 to about 2.0 g/240 ml, including about 1.5 g/240 ml.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size ranges from about 100 to about 300 ml, including from about 150 to about 250 ml, including from about 190 ml to about 240 ml.

Macronutrients

The nutritional emulsions comprise fat, protein, and carbohydrate. Generally, any source of fat, protein, and carbohydrate that is known or otherwise suitable for use in nutritional products may also be suitable for use herein, provided that such macronutrients are also compatible with the essential elements of the nutritional emulsions as defined herein.

Although total concentrations or amounts of the fat, protein, and carbohydrates may vary depending upon the nutritional needs of the intended user, such concentrations or amounts most typically fall within one of the following embodied ranges, inclusive of any other essential fat, protein, and or carbohydrate ingredients as described herein.

Carbohydrate concentrations most typically range from about 5% to about 40%, including from about 7% to about 30%, including from about 10% to about 25%, by weight of the nutritional emulsion; fat concentrations most typically range from about 1% to about 30%, including from about 2% to about 15%, and also including from about 4% to about 10%, by weight of the nutritional emulsion; and protein concentrations most typically range from about 0.5% to about 30%, including from about 1% to about 15%, and also including from about 2% to about 10%, by weight of the nutritional emulsion.

The level or amount of carbohydrates, fats, and or proteins in the nutritional compositions may also be characterized in addition to or in the alternative as a percentage of total calories in the nutritional compositions as set forth in the following table.

| Nutrient (% Calories) | Embodiment A | Embodiment B | Embodiment C |
|---|---|---|---|
| Carbohydrate | 1-98 | 10-75 | 30-50 |
| Fat | 1-98 | 20-85 | 35-55 |
| Protein | 1-98 | 5-70 | 15-35 |

Non-limiting examples of suitable fats or sources thereof for use in the nutritional emulsions described herein include coconut oil, fractionated coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, and combinations thereof.

Non-limiting examples of suitable carbohydrates or sources thereof for use in the nutritional emulsions described herein may include maltodextrin, hydrolyzed or modified starch or cornstarch, glucose polymers, corn syrup, corn syrup solids, rice-derived carbohydrates, glucose, fructose, lactose, high fructose corn syrup, honey, sugar alcohols (e.g., maltitol, erythritol, sorbitol), and combinations thereof.

Non-limiting examples of suitable protein or sources thereof for use in the nutritional emulsions include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-limiting examples of such proteins include milk protein isolates, milk protein concentrates as described herein, casein protein isolates, whey protein, sodium and calcium caseinates, whole cow's milk, partially or completely defatted milk, soy protein isolates, soy protein concentrates, and so forth.

Calcium HMB

The nutritional emulsions comprise calcium HMB, which means that the emulsions are either formulated with the addition of calcium HMB, most typically as a monohydrate, or are otherwise prepared so as to contain calcium and HMB in the finished product. Any source of HMB is suitable for use herein provided that the finished product contains calcium and HMB, although such a source is preferably calcium HMB and is most typically added as such to the nutritional emulsion during formulation.

The term "added calcium HMB" as used herein means a calcium salt of HMB, most typically as monohydrate calcium salt of HMB, as the HMB source added to the nutritional emulsion.

Although calcium HMB monohydrate is the preferred source of HMB for use herein, other suitable sources may include HMB as the free acid, a salt, an anhydrous salt, an ester, a lactone, or other product forms that otherwise provide a bioavailable form of HMB from the nutritional emulsion. Non-limiting examples of suitable salts of HMB for use herein include HMB salts, hydrated or anhydrous, of sodium, potassium, magnesium, chromium, calcium, or other non-toxic salt form. Calcium HMB monohydrate is preferred and is commercially available from Technical Sourcing International (TSI) of Salt Lake City, Utah.

The concentration of calcium HMB in the nutritional emulsions may range up to about 10%, including from about 0.1% to about 8%, and also including from about 0.2% to about 5.0%, and also including from about 0.3% to about 3%, and also including from about 0.4% to about 1.5%, by weight of the nutritional emulsion.

Soluble Protein

The nutritional emulsions of the present disclosure may comprise selected amounts or ratios of soluble protein to improve product stability and minimize the development of bitter flavors and after taste during shelf life.

The soluble protein may represent from about 50% to 100%, including from 55% to 100%, including from about 60% to about 100%, including from about 40% to about 85%, including from about 60% to about 80%, and also including from about 65% to about 75%, by weight of the total protein in the nutritional emulsion. The concentration of soluble protein may range from at least about 0.5%, including from about 1% to about 26%, and also including from about 2% to about 15%, also including from about 3% to about 10%, and also including from about 4% to about 8%, by weight of the nutritional emulsion.

The amount of soluble protein included in the nutritional emulsions may also be characterized as a weight ratio of soluble protein to calcium HMB, wherein nutritional emulsion includes a weight ratio of soluble protein to calcium HMB of at least about 3.0, including from about 4.0 to about 12.0, also including from about 6.1 to about 12, also including from about 7.0 to about 11.0, and also including from about 8.0 to about 10.0.

The term "soluble protein" as used herein, unless otherwise specified, refers to those proteins having a solubility of at least about 90% as measured in accordance with a Protein Solubility Measurement Test that includes the following steps: (1) suspend the protein at 2.00% (w/w) in water; (2) stir vigorously for one hour at 20° C. to form a suspension; (3) remove an aliquot of the suspension, and determine protein concentration as total protein; (4) centrifuge the suspension at 31,000×g and at 20° C. for one hour; (5) determine the protein concentration in the supernatant (the soluble protein); and (6) express the soluble protein as a percentage of the total protein.

Any soluble protein source is suitable for use herein provided that it meets the solubility requirement as defined herein, some non-limiting examples of which include sodium caseinate (>95% solubility as determined by the Protein Solubility Measurement Test), whey protein concentrate (>90% solubility as determined by the Protein Solubility Measurement Test), and combinations thereof. Non-soluble proteins may of course also be included in the nutritional emulsions provided that the remaining soluble protein component is represented in accordance with the requirements as set forth herein.

Soluble protein suitable for use herein may also be characterized by the content of phosphoserine in the protein, wherein the soluble proteins in this context are defined as those proteins having at least about 100 mmoles, including from about 150 to 400 mmoles, including from about 200 to about 350 mmoles, and also including from about 250 to about 350 mmoles, of phosphoserine per kilogram of protein.

When the soluble protein is defined in terms of phosphoserine content, it has been found that the weight ratio of the soluble protein (with the defined phosphoserine content) to the calcium HMB may be at least about 3:1, including at least about 5:1, and also including at least about 7:1, and also including from about 9:1 to about 30:1. In this context, the proteins having the requisite content of phosphoserine are most typically in the form of monovalent caseinate salts such as sodium caseinate, potassium caseinate, and combinations thereof.

In one embodiment, the soluble protein may also be characterized by a mole ratio of monovalent caseinate phosphoserine to calcium HMB monohydrate of least about 0.2, including from about 0.2 to about 2.0, and also including from about 0.25 to 1.7.

It should be understood, however, that any phosphoserine-containing protein may be suitable for use herein provided that it has the requisite phosphoserine content and that the phosphoserine used in calculating the ratios are not bound, complexed, or otherwise attached to a polyvalent cation such as calcium or magnesium.

It should also be noted that alternative definitions as described herein for soluble proteins may include proteins that have little or no phosphoserine content, so that the soluble protein fraction of the compositions may include soluble protein with and/or without phosphoserine. The soluble protein for use herein may therefore be defined by any one or more of the soluble protein characterizations, separately or in combination.

The phosphoserine moieties within the protein may therefore be available for binding with the calcium released from the calcium HMB so that the above ratios of soluble protein to calcium HMB are the ratio of protein with phosphoserine moities that are unbound, unattached, or otherwise available to bind soluble calcium from the calcium HMB during formulation. It could be, for example, that a mixture of calcium caseinate and sodium caseinate are used in the composition, but the ratio of proteins defined by a phosphoserine content to calcium HMB is calculated based on the protein fraction from the sodium caseinate and additionally any protein from the calcium caseinate fraction that is not bound to calcium.

Soluble Calcium Binding Capacity

The nutritional emulsions may comprise a selected weight ratio of a soluble calcium binding capacity (SCBC) to the total soluble calcium in the emulsion to improve product stability and minimize the development over time of bitter flavors and after taste.

The ratio of the soluble calcium binding capacity (defined herein) to total soluble calcium of the nutritional emulsions is a weight ratio of at least about 2.3, including from about 2.3 to about 12.0, also including from about 3.0 to about 8.0, and also including from about 4.0 to about 6.5, wherein the ratio is determined in accordance with the following formulas:

Ratio=SCBC/[soluble calcium]

SCBC=(0.32×[soluble citrate]+0.63[soluble phosphate]+0.013×[soluble protein])

The weight ratio of SCBC to the concentration of total soluble calcium can be adjusted to minimize the concentration of unbound calcium in the nutritional emulsion, or to minimize the weight ratio of such unbound calcium to HMB in the emulsions, to improve product stability and reduce the development over time of bitter flavors and after tastes.

The nutritional emulsions of the present disclosure comprise calcium as a desirable ingredient in the nutritional emulsions suitable for use in developing or maintaining of healthy muscle in targeted individuals. Some or all of the calcium may be provided by the addition of calcium HMB as described herein. Any other calcium source, however, may be used provided that such other source is compatible with the essential elements of the nutritional emulsions.

The concentration of calcium in the nutritional emulsions typically exceeds about 10 mg/L, and may also include concentrations of from about 25 mg/L to about 3000 mg/L, also including from about 50 mg/L to about 500 mg/L, and also including from about 100 mg/L to about 300 mg/L.

To minimize the taste and stability issues in the nutritional emulsions, the calcium is formulated so as to minimize the extent to which the calcium is solubilized in the emulsions. As such, solubilized calcium concentrations in the nutritional emulsions may be less than about 900 mg/L, including less than about 700 mg/L, also including from about 500 mg/L to about 700 mg/L, and also including from about 400 mg/L to about 600 mg/L. In this context, the term "solubilized calcium" refers to free, ionized or supernatant calcium in the nutritional emulsion as measured at 20° C.

The calcium in the nutritional emulsions may also be characterized by a ratio (on an equivalents basis) of solubilized citrate to solubilized calcium of not more than 5.0, including not more than 4.0, also including not more than 3.0, and also including from about 0.8 to about 3.0. In this context, the terms "solubilized citrate" and "solubilized calcium" refers to the equivalents of citrate and calcium cations, respectively, present in supernatants of the nutritional emulsion as measured at 20° C.

The calcium component of the nutritional emulsion may also be characterized by a solubilized calcium level that represents less than 900 mg/L, including less than 700 mg/L, and also including less than 600 mg/L, and also including from 400 mg/L to 700 mg/L of the nutritional emulsion, wherein the weight ratio of calcium HMB to the solubilized calcium ranges from about 6:1 to about 15:1, including from about 6:1 to about 12:1 also including from about 6:1 to about 10:1 and also including from about 6:1 to about 8:1.

Vitamin D

The nutritional emulsions of the present disclosure may further comprise vitamin D to help maintain healthy muscle in the targeted user. Vitamin D forms include Vitamin D2 (ergocalciferol) and Vitamin D3 (cholecalciferol) or other forms suitable for use in a nutritional product.

The amount of Vitamin D in the nutritional emulsion most typically ranges up to about 1000 IU, more typically from about 10 to about 600 IU, and more typically from about 50 to 400 IU per serving.

Optional Ingredients

The nutritional emulsions described herein may further comprise other optional ingredients that may modify the physical, chemical, hedonic or processing characteristics of the products or serve as pharmaceutical or additional nutritional components when used in the targeted population. Many such optional ingredients are known or otherwise suitable for use in other nutritional products and may also be used in the nutritional emulsions described herein, provided that such optional ingredients are safe and effective for oral administration and are compatible with the essential and other ingredients in the selected product form.

Non-limiting examples of such optional ingredients include preservatives, antioxidants, emulsifying agents, buffers, pharmaceutical actives, additional nutrients as described herein, colorants, flavors, thickening agents and stabilizers, and so forth.

The nutritional emulsions may further comprise vitamins or related nutrients, non-limiting examples of which include vitamin A, vitamin E, vitamin K, thiamine, riboflavin, pyridoxine, vitamin B12, carotenoids, niacin, folic acid, pantothenic acid, biotin, vitamin C, choline, inositol, salts, and derivatives thereof, and combinations thereof.

The nutritional emulsion may further comprise minerals, non-limiting examples of which include phosphorus, magnesium, iron, zinc, manganese, copper, sodium, potassium, molybdenum, chromium, selenium, chloride, and combinations thereof.

The nutritional emulsions may also include one or more masking agents to reduce or otherwise obscure the development of any residual bitter flavors and after taste in the emulsions over time. Suitable masking agents include natural and artificial sweeteners, sodium sources such as sodium chloride, and hydrocolloids, such as guar gum, xanthan gum, carrageenan, gellan gum, and combinations thereof. The amount of masking agent in the nutritional emulsion may vary depending upon the particular masking agent selected, other ingredients in the formulation, and other formulation or product target variables. Such amounts, however, most typically range from at least about 0.1%, including form about 0.15% to about 3.0%, and also including from about 0.18% to about 2.5%, by weight of the nutritional emulsion.

Method of Use

The nutritional emulsions described herein are useful to provide supplement, primary, or sole sources of nutrition, and or to provide individuals one or more benefits as described herein. In accordance with such methods, the emulsions may be administered orally as needed to provide the desired level of nutrition, most typically in the form of one to two servings daily, in one or two or more divided doses daily, e.g., serving sizes typically ranging from about 100 to about 300 ml, including from about 150 to about 250 ml, including from about 190 ml to about 240 ml, wherein each serving contains from about 0.4 to about 3.0 g, including from about 0.75 to about 2.0 g, including about 1.5 g, of calcium HMB per serving.

Such methods are further directed to provide the individual upon administration of such products, most typically after daily use over an extended period of time of from about 1 to about 6 months, including from about 1 to about 3 months, one or more of 1) to support maintenance of lean body mass, 2) to support of strength and or muscle strength, 3) to decrease protein breakdown and damage of muscle cells, and 4) to help with muscle recovery following exercise or other trauma, and 5) to reduce muscle protein breakdown following exercise.

Such methods are also helpful to achieve one or more of 1) to maintain and support lean body mass in elderly with sarcopenia, 2) to provide nutrition to support an active and independent lifestyle in individuals, especially in the elderly, 3) to support recovery of muscle strength, 4) to help rebuild muscle and regain strength, and 5) to improve strength, including muscle strength, and mobility.

Methods of Manufacture

The nutritional emulsions for use herein may be manufactured by any known or otherwise suitable method for making nutritional emulsions, including milk-based nutritional emulsions.

In one suitable manufacturing process, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the selected oils (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. Avicel, gellan, carrageenan), and calcium HMB or other HMB source. The resulting CHO-MIN slurry is held for 10 minutes with continued heat and agitation before adding additional minerals (e.g., potassium chloride, magnesium carbonate, potassium iodide, etc.) and/or carbohydrates (e.g., frucotooligosaccharide, sucrose, corn syrup, etc.). The PIW slurry is then formed by mixing with heat and agitation the remaining protein (e.g., sodium caseineate, soy protein concentrate, etc.) into water.

The resulting slurries are then blended together with heated agitation and the pH adjusted to the desired range, typically from 6.6-7.0, after which the composition is subjected to high-temperature short-time (HTST) processing during which the composition is heat treated, emulsified and homogenized, and then allowed to cool. Water soluble vitamins and ascorbic acid are added, the pH is again adjusted to the desired range if necessary, flavors are added, and water is added to achieve the desired total solid level. The composition is then aseptically packaged to form an aseptically packaged nutritional emulsion, or the composition is added to retort stable containers and then subjected to retort sterilization to form retort sterilized nutritional emulsions.

The manufacturing processes for the nutritional emulsions may be carried out in ways other than those set forth herein without departing from the spirit and scope of the present invention. The present embodiments are, therefore, to be considered in all respects illustrative and not restrictive and that all changes and equivalents also come within the description of the present disclosure.

EXAMPLES

The following examples illustrate specific embodiments and or features of the nutritional emulsions of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional emulsions prepared in accordance with the manufacturing methods described herein, such that each exemplified composition, unless otherwise specified, includes an aseptically processed embodiment and a retort packaged embodiment. These compositions are aqueous oil-in-water emulsions that are packaged in 240 ml plastic containers and remain physically stable for 12-18 months after formulation/packaging at storage temperatures ranging from 1-25° C. The packaged emulsions likewise remain pH stable over time and do not develop an excessively bitter flavor or aftertaste during the storage.

Examples 1-4

Examples 1-4 illustrate nutritional emulsions of the present disclosure, the ingredients of which are listed in the table below. All ingredient amounts are listed as kilogram per 1000 kilogram batch of product, unless otherwise specified.

| Ingredient | Example 1 | Example 2 | Example 3 | Example 4 |
|---|---|---|---|---|
| Water | Q.S | Q.S. | Q.S. | Q.S. |
| Maltodextrin DE 9-12 | 120.0 | 120.0 | 120.0 | 120.0 |
| Sucrose | 71.38 | 71.38 | 71.38 | 71.38 |
| Milk Protein Concentrate | 18.65 | 18.65 | 18.65 | 18.65 |
| Canola Oil | 27.5 | 27.5 | 27.5 | 27.5 |
| Sodium Caseinate | 26.68 | 26.68 | 26.68 | 26.68 |
| Soy Protein Concentrate | 14.05 | 14.05 | 14.05 | 14.05 |
| Corn Oil | 15.70 | 15.70 | 15.70 | 15.70 |
| Calcium HMB monohydrate | 6.00 | 6.5 | 7.0 | 4 |
| Whey Protein Concentrate | 3.50 | 3.50 | 3.50 | 3.50 |
| Magnesium Phosphate | 1.92 | 1.92 | 1.92 | 1.92 |

-continued

| Ingredient | Example 1 | Example 2 | Example 3 | Example 4 |
|---|---|---|---|---|
| Potassium Citrate | 6.92 | 6.92 | 6.92 | 6.92 |
| Sodium Citrate | 0.903 | 0.903 | 0.903 | 0.903 |
| Lecithin | 1.50 | 1.50 | 1.50 | 1.50 |
| Sodium Tripolyphosphate | 1.06 | 1.06 | 1.06 | 1.06 |
| Potassium Phosphate dibasic | 0.730 | 0.730 | 0.730 | 0.730 |
| Potassium Chloride | 1.04 | 1.04 | 1.04 | 1.04 |
| Ascorbic Acid | 0.235 | 0.235 | 0.235 | 0.235 |
| Carrageenan | 0.150 | 0.150 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Gellan Gum | 0.050 | 0.050 | 0.050 | 0.050 |
| Vitamin A, D, E Premix | 0.0758 | 0.0758 | 0.0758 | 0.0758 |
| Water sol. Vitamin premix | 0.0728 | 0.0728 | 0.0728 | 0.0728 |
| Potassium Iodide | 0.00022 | 0.00022 | 0.00022 | 0.00022 |
| Chromium Chloride | 0.000217 | 0.000217 | 0.000217 | 0.000217 |
| Flavor | 3.3 | 3.3 | 3.3 | 3.3 |
| Features | | | | |
| Soluble protein/total protein (wt/wt) | 59% | 58% | 57% | 50% |
| Soluble protein/calcium HMB (wt/wt) | 6.2 | 5.6 | 5.1 | 7.5 |
| Solubilized calcium (wt %) | 0.045% | 0.049% | 0.053% | 0.070% |
| SCBC/Solubilized calcium (wt/wt) | 5.5 | 5.0 | 4.5 | 3.0 |
| Solubilized citrate/solubilized calcium (equiv) | 3.5 | 3.0 | 2.5 | 1.5 |

Examples 5-8

Examples 5-8 illustrate nutritional emulsions of the present disclosure, the ingredients of which are listed in the table below. All ingredient amounts are listed as kg per 1000 kg batch of product, unless otherwise specified.

| Ingredient | Example 5 | Example 6 | Example7 | Example 8 |
|---|---|---|---|---|
| Water | Q.S | Q.S. | Q.S. | Q.S. |
| Maltodextrin DE 9-12 | 120.0 | 120.0 | 120.0 | 120.0 |
| Sucrose | 71.38 | 71.38 | 71.38 | 71.38 |
| Milk Protein Concentrate | 14.65 | 13.65 | 12.65 | 11.65 |
| Canola Oil | 27.5 | 27.5 | 27.5 | 27.5 |
| Sodium Caseinate | 30.68 | 31.68 | 32.68 | 33.68 |
| Soy Protein Concentrate | 14.05 | 14.05 | 14.05 | 14.05 |
| Corn Oil | 15.70 | 15.70 | 15.70 | 15.70 |
| Calcium HMB monohydrate | 6.00 | 6.5 | 7.0 | 7.5 |
| Whey Protein Concentrate | 3.50 | 3.50 | 3.50 | 3.50 |
| Magnesium Phosphate | 1.92 | 1.92 | 1.92 | 1.92 |
| Potassium Citrate | 6.92 | 6.92 | 6.92 | 6.92 |
| Sodium Citrate | 0.903 | 0.903 | 0.903 | 0.903 |
| Lecithin | 1.50 | 1.50 | 1.50 | 1.50 |
| Sodium Tripolyphosphate | 1.06 | 1.06 | 1.06 | 1.06 |
| Potassium Phosphate dibasic | 0.730 | 0.730 | 0.730 | 0.730 |
| Potassium Chloride | 1.04 | 1.04 | 1.04 | 1.04 |
| Ascorbic Acid | 0.235 | 0.235 | 0.235 | 0.235 |
| Carrageenan | 0.150 | 0.150 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Gellan Gum | 0.050 | 0.050 | 0.050 | 0.050 |
| Vitamin A, D, E Premix | 0.0758 | 0.0758 | 0.0758 | 0.0758 |
| Water sol. Vitamin premix | 0.0728 | 0.0728 | 0.0728 | 0.0728 |
| Potassium Iodide | 0.00022 | 0.00022 | 0.00022 | 0.00022 |
| Chromium Chloride | 0.000217 | 0.000217 | 0.000217 | 0.000217 |
| Flavor | 3.3 | 3.3 | 3.3 | 3.3 |
| Features | | | | |
| Soluble protein/total protein (wt/wt) | 63% | 64% | 65% | 66% |
| Soluble protein/calcium HMB (wt/wt) | 6.6 | 6.2 | 5.8 | 5.0 |
| Solubilized calcium (wt %) | 0.045% | 0.049% | 0.053% | 0.070% |
| SCBC/Solubilized calcium (wt/wt) | 5.5 | 5.0 | 4.5 | 3.0 |

-continued

| Ingredient | Example 5 | Example 6 | Example 7 | Example 8 |
|---|---|---|---|---|
| Solubilized citrate/solubilized calcium (equiv) | 3.5 | 3.0 | 2.5 | 1.5 |

Examples 9-12

Examples 9-12 illustrate nutritional emulsions of the present disclosure, the ingredients of which are listed in the table below. All ingredient amounts are listed as kilogram per 1000 kilogram batch of product, unless otherwise specified.

| Ingredient | Example 9 | Example 10 | Example 11 | Example 12 |
|---|---|---|---|---|
| Water | Q.S | Q.S. | Q.S. | Q.S. |
| Maltodextrin DE 9-12 | 120.0 | 120.0 | 120.0 | 120.0 |
| Sucrose | 71.38 | 71.38 | 71.38 | 71.38 |
| Milk Protein Concentrate | 0.00 | 0.00 | 8.65 | 10.65 |
| Canola Oil | 27.5 | 27.5 | 27.5 | 27.5 |
| Sodium Caseinate | 45.33 | 45.33 | 36.68 | 34.68 |
| Soy Protein Concentrate | 0.00 | 0.00 | 12.05 | 9.05 |
| Corn Oil | 15.70 | 15.70 | 15.70 | 15.70 |
| Calcium HMB monohydrate | 6.0 | 6.5 | 7.0 | 8.0 |
| Whey Protein Concentrate | 17.55 | 17.55 | 5.50 | 8.50 |
| Magnesium Phosphate | 1.92 | 1.92 | 1.92 | 1.92 |
| Potassium Citrate | 6.92 | 6.92 | 6.92 | 6.92 |
| Sodium Citrate | 0.903 | 0.903 | 0.903 | 0.903 |
| Lecithin | 1.50 | 1.50 | 1.50 | 1.50 |
| Sodium Tripolyphosphate | 1.06 | 1.06 | 1.06 | 1.06 |
| Potassium Phosphate dibasic | 0.730 | 0.730 | 0.730 | 0.730 |
| Potassium Chloride | 1.04 | 1.04 | 1.04 | 1.04 |
| Ascorbic Acid | 0.235 | 0.235 | 0.235 | 0.235 |
| Carrageenan | 0.150 | 0.150 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Gellan Gum | 0.050 | 0.050 | 0.050 | 0.050 |
| Vitamin A, D, E Premix | 0.0758 | 0.0758 | 0.0758 | 0.0758 |
| Water sol. Vitamin premix | 0.0728 | 0.0728 | 0.0728 | 0.0728 |
| Potassium Iodide | 0.00022 | 0.00022 | 0.00022 | 0.00022 |
| Chromium Chloride | 0.000217 | 0.000217 | 0.000217 | 0.000217 |
| Flavor | 3.3 | 3.3 | 3.3 | 3.3 |
| Features | | | | |
| Soluble protein/total protein (wt/wt) | 94% | 93% | 71% | 73% |
| Soluble protein/calcium HMB (wt/wt) | 9.8 | 9.0 | 6.4 | 5.1 |
| Solubilized calcium (wt %) | 0.045% | 0.050% | 0.058% | 0.070% |
| SCBC/Solubilized calcium (wt/wt) | 10 | 8.8 | 5.9 | 3.8 |
| Solubilized citrate/solubilized calcium (equiv) | 3.8 | 3.4 | 2.9 | 1.5 |

Examples 13-16

Examples 13-16 illustrate nutritional emulsions of the present disclosure, the ingredients of which are listed in the table below. All ingredient amounts are listed as kilogram per 1000 kilogram batch of product, unless otherwise specified.

| Ingredient | Example 13 | Example 14 | Example 15 | Example 16 |
|---|---|---|---|---|
| Water | Q.S | Q.S. | Q.S. | Q.S. |
| Sucrose | 96.05 | 96.05 | 96.05 | 96.05 |
| Maltodextrin DE 5 | 16.46 | 16.46 | 16.46 | 16.46 |
| Milk Protein Concentrate | 18.95 | 0.00 | 8.95 | 25.00 |
| Soy Oil | 13.31 | 13.31 | 13.31 | 13.31 |
| Fructooligosaccharides | 8.69 | 8.69 | 8.69 | 8.69 |
| Soy Protein Concentrate | 13.80 | 0.00 | 10.80 | 5.92 |
| Canola Oil | 5.32 | 5.32 | 5.32 | 5.32 |
| Sodium Caseinate | 25.64 | 58.39 | 61.39 | 28.00 |

| Ingredient | Example 13 | Example 14 | Example 15 | Example 16 |
|---|---|---|---|---|
| Corn Oil | 11.70 | 11.70 | 11.70 | 11.70 |
| Calcium HMB monohydrate | 6.70 | 7.00 | 2.50 | 5.00 |
| Dietary Fiber | 4.51 | 4.51 | 4.51 | 4.51 |
| Whey Protein Concentrate | 3.44 | 3.44 | 13.44 | 2.92 |
| Potassium Citrate | 4.48 | 4.48 | 4.48 | 4.48 |
| Flavor | 2.00 | 2.00 | 2.00 | 2.00 |
| Magnesium Phosphate | 2.75 | 2.75 | 2.75 | 2.75 |
| Lecithin | 1.50 | 1.50 | 1.50 | 1.50 |
| Di sodium Phosphate Dihyd | 0.436 | 0.436 | 0.436 | 0.436 |
| Potassium Phosphate Dibasic | 0.556 | 0.556 | 0.556 | 0.556 |
| Sodium Chloride | 0.498 | 0.498 | 0.498 | 0.498 |
| Choline Chloride | 0.480 | 0.480 | 0.480 | 0.480 |
| Ascorbic Acid | 0.465 | 0.465 | 0.465 | 0.465 |
| Carrageenan | 0.300 | 0.300 | 0.300 | 0.300 |
| Trace/Ultra Trace minerals | 0.420 | 0.420 | 0.420 | 0.420 |
| Potassium Chloride | 0.698 | 0.698 | 0.698 | 0.698 |
| Potassium Hydroxide | 0.321 | 0.321 | 0.321 | 0.321 |
| L-carnitine | 0.180 | 0.180 | 0.180 | 0.180 |
| Water soluble Vitamin Premix | 0.07269 | 0.07269 | 0.07269 | 0.07269 |
| Vitamin DEK premix | 0.128 | 0.128 | 0.128 | 0.128 |
| Gellan Gum | 0.050 | 0.050 | 0.050 | 0.050 |
| Vitamin A Palmitate | 0.008245 | 0.008245 | 0.008245 | 0.008245 |
| Vitamin D3 | 0.000399 | 0.000399 | 0.000399 | 0.000399 |
| Potassium Iodide | 0.000194 | 0.000194 | 0.000194 | 0.000194 |
| Features | | | | |
| Soluble protein/total protein (wt/wt) | 58% | 95% | 80% | 61% |
| Soluble protein/calcium HMB (wt/wt) | 5.4 | 8.4 | 30 | 15 |
| Solubilized calcium (wt %) | 0.050% | 0.060% | 0.080% | 0.055% |
| SCBC/Solubilized calcium (wt/wt) | 4.4 | 9.7 | 8.8 | 4.9 |
| Solubilized citrate/solubilized calcium (equiv) | 1.3 | 3.1 | 2.7 | 2.9 |

Examples 17-20

Examples 17-20 illustrate nutritional emulsions of the present disclosure, the ingredients of which are listed in the table below. All ingredient amounts are listed as kilogram per 1000 kilogram batch of product, unless otherwise specified.

| Ingredient | Example 17 | Example 18 | Example 19 | Example 20 |
|---|---|---|---|---|
| Water | Q.S | Q.S. | Q.S. | Q.S. |
| Sucrose | 96.05 | 96.05 | 96.05 | 96.05 |
| Maltodextrin DE 5 | 16.46 | 16.46 | 16.46 | 16.46 |
| Milk Protein Concentrate | 24.98 | 0.00 | 25.00 | 10.00 |
| Soy Oil | 13.31 | 13.31 | 13.31 | 13.31 |
| Fructooligosaccharides | 8.69 | 8.69 | 8.69 | 8.69 |
| Soy Protein Concentrate | 13.64 | 0.00 | 5.87 | 10.64 |
| Canola Oil | 5.32 | 5.32 | 5.32 | 5.32 |
| Sodium Caseinate | 25.64 | 58.39 | 61.39 | 28.00 |
| Com Oil | 11.70 | 11.70 | 11.70 | 11.70 |
| Calcium HMB monohydrate | 6.50 | 3.5 | 4.25 | 7.5 |
| Dietary Fiber | 4.51 | 4.51 | 4.51 | 4.51 |
| Whey Protein Concentrate | 3.40 | 17.04 | 6.87 | 6.40 |
| Potassium Citrate | 4.48 | 4.48 | 4.48 | 4.48 |
| Flavor | 2.00 | 2.00 | 2.00 | 2.00 |
| Magnesium Phosphate | 2.75 | 2.75 | 2.75 | 2.75 |
| Lecithin | 1.50 | 1.50 | 1.50 | 1.50 |
| Di sodium Phosphate Dihyd | 0.436 | 0.436 | 0.436 | 0.436 |
| Potassium Phosphate Dibasic | 0.556 | 0.556 | 0.556 | 0.556 |
| Sodium Chloride | 0.498 | 0.498 | 0.498 | 0.498 |
| Choline Chloride | 0.480 | 0.480 | 0.480 | 0.480 |
| Ascorbic Acid | 0.465 | 0.465 | 0.465 | 0.465 |
| Carrageenan | 0.300 | 0.300 | 0.300 | 0.300 |
| Trace/Ultra Trace minerals | 0.420 | 0.420 | 0.420 | 0.420 |
| Potassium Chloride | 0.698 | 0.698 | 0.698 | 0.698 |
| Potassium Hydroxide | 0.321 | 0.321 | 0.321 | 0.321 |
| L-carnitine | 0.180 | 0.180 | 0.180 | 0.180 |
| Water soluble Vitamin Premix | 0.07269 | 0.07269 | 0.07269 | 0.07269 |

-continued

| Ingredient | Example 17 | Example 18 | Example 19 | Example 20 |
|---|---|---|---|---|
| Vitamin DEK premix | 0.128 | 0.128 | 0.128 | 0.128 |
| Gellan Gum | 0.050 | 0.050 | 0.050 | 0.050 |
| Vitamin A Palmitate | 0.008245 | 0.008245 | 0.008245 | 0.008245 |
| Vitamin D3 | 0.000399 | 0.000399 | 0.000399 | 0.000399 |
| Potassium Iodide | 0.000194 | 0.000194 | 0.000194 | 0.000194 |
| Features | | | | |
| Soluble protein/total protein (wt/wt) | 56% | 94% | 74% | 68% |
| Soluble protein/calcium HMB (wt/wt) | 5.8 | 20 | 17 | 5.0 |
| Solubilized calcium (wt %) | 0.057% | 0.085% | 0.079% | 0.060% |
| SCBC/Solubilized calcium (wt/wt) | 2.9 | 7.9 | 6.8 | 4.7 |
| Solubilized citrate/solubilized calcium (equiv) | 3.0 | 0.9 | 1.5 | 2.2 |

What is claimed is:

1. A shelf stable nutritional emulsion comprising protein, carbohydrate, fat, and from about 0.1% to about 10% of calcium HMB by weight of the nutritional emulsion,
   wherein the nutritional emulsion comprises at least one of a soluble citrate, a soluble phosphate, and a soluble protein, such that:
   i) the nutritional emulsion has a weight ratio of a soluble calcium binding capacity to soluble calcium of from about 2.3 to about 12.0, and
   ii) the soluble calcium binding capacity=0.32[soluble citrate]+0.63[soluble phosphate]+0.013[soluble protein],
   wherein the nutritional emulsion remains physically stable for 12 to 18 months, at a storage temperature of from 1° C. to 25° C., after formulation and packaging and
   wherein the nutritional emulsion has a pH from about 5.5 to about 8.

2. The nutritional emulsion of claim 1, wherein the weight ratio of the soluble calcium binding capacity to the soluble calcium is from about 3.0 to about 8.0.

3. The nutritional emulsion of claim 1, wherein the weight ratio of the soluble calcium binding capacity to the soluble calcium is from about 4.0 to about 6.5.

4. The nutritional emulsion of claim 1, wherein the soluble protein constitutes from about 50% to 100% by weight of total protein in the nutritional emulsion.

5. The nutritional emulsion of claim 1, wherein the soluble protein constitutes from about 55% to 100% by weight of total protein in the nutritional emulsion, and wherein the soluble protein includes a phosphoserine-containing protein having at least about 100 mmoles of phosphoserine per kilogram of the phosphoserine-containing protein.

6. The nutritional emulsion of claim 5, wherein the soluble protein constitutes from about 60% to about 80% by weight of total protein in the nutritional emulsion.

7. The nutritional emulsion of claim 4, wherein the soluble protein consists of at least one of sodium caseinate and whey protein concentrate.

8. The nutritional emulsion of claim 4, wherein the soluble protein constitutes from about 2% to about 15% by weight of the nutritional emulsion.

9. The nutritional emulsion of claim 1, wherein the nutritional emulsion is packaged in a hermetically sealed container and is shelf stable at a storage temperature of from 18° C. to 24° C. for 3 months to 6 months.

10. A shelf stable nutritional emulsion comprising protein, carbohydrate, fat, and from about 0.1% to about 10% of calcium HMB by weight of the nutritional emulsion,
    wherein the nutritional emulsion comprises less than 900 mg/L of soluble calcium in a weight ratio of the calcium HMB to the soluble calcium of from about 6:1 to about 15:1,
    wherein the nutritional emulsion remains physically stable for 12 to 18 months, at a storage temperature of from 1° C. to 25° C., after formulation and packaging, and
    wherein the nutritional emulsion has a pH from about 5.5 to about 8.

11. The nutritional emulsion of claim 10, wherein the nutritional emulsion comprises less than 700 mg/L of the soluble calcium.

12. The nutritional emulsion of claim 10, wherein the nutritional emulsion comprises from about 400 mg/L to about 700 mg/L of the soluble calcium.

13. The nutritional emulsion of claim 10, wherein the weight ratio of the calcium HMB to the soluble calcium is from about 6:1 to about 12:1.

14. The nutritional emulsion of claim 10, wherein the weight ratio of the calcium HMB to the soluble calcium is from about 6:1 to about 8:1.

15. The nutritional emulsion of claim 10, wherein the nutritional emulsion includes soluble protein in an amount of from about 50% to 100% by weight of the total protein.

16. The nutritional emulsion of claim 15, wherein the soluble protein consists of at least one of sodium caseinate and whey protein concentrate.

17. The nutritional emulsion of claim 15, wherein the nutritional emulsion includes the soluble protein in an amount of from about 55% to 100% by weight of the total protein and includes a phosphoserine-containing protein having at least about 100 mmoles of phosphoserine per kilogram of the phosphoserine-containing protein.

18. The nutritional emulsion of claim 10, wherein the nutritional emulsion includes soluble protein in an amount of from about 60% to about 85% by weight of the total protein.

* * * * *